(12) United States Patent
Jeong et al.

(10) Patent No.: US 12,364,728 B2
(45) Date of Patent: Jul. 22, 2025

(54) COMPOSITION FOR REDUCING BODY FAT COMPRISING GREEN TEA EXTRACT CONTAINING GALLOCATECHIN GALLATE AS AN ACTIVE INGREDIENT AND MANUFACTURING METHOD THEREOF

(71) Applicant: AMOREPACIFIC CORPORATION, Seoul (KR)

(72) Inventors: Hyun Woo Jeong, Yongin-si (KR); Si Young Cho, Yongin-si (KR); Yong Deog Hong, Yongin-si (KR); Wanki Kim, Yongin-si (KR); Miyoung Park, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 136 days.

(21) Appl. No.: 17/570,765

(22) Filed: Jan. 7, 2022

(65) Prior Publication Data
US 2022/0218778 A1    Jul. 14, 2022

(30) Foreign Application Priority Data
Jan. 11, 2021    (KR) .......................... 10-2021-0003451

(51) Int. Cl.
| | | |
|---|---|---|
| *A61K 36/82* | (2006.01) | |
| *A61K 9/00* | (2006.01) | |
| *A61K 9/16* | (2006.01) | |
| *A61K 9/20* | (2006.01) | |
| *A61K 31/352* | (2006.01) | |
| *A61P 3/04* | (2006.01) | |

(52) U.S. Cl.
CPC ............ *A61K 36/82* (2013.01); *A61K 9/0019* (2013.01); *A61K 9/0095* (2013.01); *A61K 9/1623* (2013.01); *A61K 9/2013* (2013.01); *A61K 9/2018* (2013.01); *A61K 9/2059* (2013.01); *A61K 31/352* (2013.01); *A61P 3/04* (2018.01)

(58) Field of Classification Search
None
See application file for complete search history.

(56) References Cited

U.S. PATENT DOCUMENTS

| | | | |
|---|---|---|---|
| 5,318,986 | A | 6/1994 | Hara et al. |
| 7,939,559 | B2 | 5/2011 | Nakai et al. |
| 9,414,613 | B2 | 8/2016 | Sato et al. |
| 9,968,109 | B2 | 5/2018 | Shimoda et al. |
| 10,172,371 | B2 | 1/2019 | Shimoda |
| 10,537,605 | B2 | 1/2020 | Ling |
| 2007/0116788 | A1* | 5/2007 | Murase ................. A61K 31/35 514/456 |
| 2008/0261897 | A1 | 10/2008 | Dorr et al. |
| 2012/0035254 | A1 | 2/2012 | Enokuchi et al. |
| 2019/0328020 | A1 | 10/2019 | Yamamoto et al. |
| 2020/0323942 | A1* | 10/2020 | Kim ..................... A61K 9/0095 |
| 2021/0113517 | A1 | 4/2021 | Tamura et al. |

FOREIGN PATENT DOCUMENTS

| | | |
|---|---|---|
| CN | 100384412 C | 4/2008 |
| CN | 1980655 B | 2/2011 |
| CN | 1939296 B | 4/2011 |
| CN | 101869633 B | 1/2013 |
| CN | 102388031 B | 12/2014 |
| CN | 101484158 B | 9/2015 |
| CN | 107865149 A | 4/2018 |
| CN | 108514119 A | 9/2018 |
| CN | 109123627 A | 1/2019 |
| CN | 109770145 A | 5/2019 |
| CN | 110087648 A | 8/2019 |
| CN | 110151752 A | 8/2019 |
| CN | 110663788 A | 1/2020 |
| CN | 110839890 A | 2/2020 |
| CN | 111035697 A | 4/2020 |
| CN | 111514129 A | 8/2020 |
| EP | 0522502 A1 | 1/1993 |
| EP | 3603628 A1 | 2/2020 |
| KR | 10-1993-0001925 A | 2/1993 |
| KR | 10-0178522 B1 | 3/1999 |
| KR | 10-0592796 B1 | 6/2006 |
| KR | 20080006895 A * | 1/2008 |
| KR | 10-1376125 B1 | 3/2014 |
| KR | 10-1381590 B1 | 4/2014 |
| KR | 10-1414410 B1 | 7/2014 |
| KR | 10-2015-0105563 A | 9/2015 |
| KR | 10-1721389 B1 | 3/2017 |
| KR | 10-2017-0109875 A | 10/2017 |
| KR | 10-1899277 B1 | 9/2018 |

(Continued)

OTHER PUBLICATIONS

Unit converter, 2024 (Year: 2024).*

*Primary Examiner* — Robert A Wax
*Assistant Examiner* — William Craigo
(74) *Attorney, Agent, or Firm* — Merchant & Gould P.C.

(57) ABSTRACT

The present disclosure relates to a composition for reducing body fat, which contains a green tea extract containing 4 wt % or more of gallocatechin gallate based on the total weight of the extract as an active ingredient, and a method for preparing the same. The composition according to the present disclosure provides a superior effect of reducing body fat as the green tea extract containing gallocatechin gallate is contained as an active ingredient. Accordingly, it can provide substances effective for treating obesity through various researches.

13 Claims, 18 Drawing Sheets

(56) References Cited

FOREIGN PATENT DOCUMENTS

| | | |
|---|---|---|
| KR | 10-1923840 B1 | 2/2019 |
| KR | 10-1983871 B1 | 5/2019 |
| KR | 10-2019-0095423 A | 8/2019 |
| KR | 10-2019-0134671 A | 12/2019 |
| KR | 10-2020-0046418 A | 5/2020 |
| KR | 10-2020-0100028 A | 8/2020 |
| KR | 10-2020-0108399 A | 9/2020 |
| WO | 96/37201 A2 | 11/1996 |
| WO | 2013175253 A1 | 11/2013 |
| WO | 2019/018774 A1 | 1/2019 |
| WO | WO-2019088412 A1 * | 5/2019 ........... A23L 33/105 |

* cited by examiner

COMPOSITION FOR REDUCING BODY FAT COMPRISING GREEN TEA EXTRACT CONTAINING GALLOCATECHIN GALLATE AS AN ACTIVE INGREDIENT AND MANUFACTURING METHOD THEREOF

CROSS-REFERENCE TO RELATED APPLICATION

This application claims the priority of Korean Patent Application No. 10-2021-0003451, filed on Jan. 11, 2021, and all the benefits accruing therefrom under 35 U.S.C. § 119, the contents of which in their entirety are herein incorporated by reference.

TECHNICAL FIELD

Disclosed in the present specification are a composition for reducing body fat, which contains a green tea extract containing gallocatechin gallate as an active ingredient, and a method for preparing the same.

BACKGROUND ART

Obesity is a medical condition in which excess energy has been accumulated as body fat due to imbalance between the energy intake as food and the energy expenditure through physical activity. It refers to the state where the number or size of adipocytes in adipose tissue has increased. It is known that obesity is also caused by various factors including genetic factors, environmental factors including westernized diet, psychological factors, energy metabolism disorders, etc. If the obesity persists for a long time, metabolic diseases and adult diseases such as diabetes, hyperlipidemia, heart disease, stroke, arteriosclerosis, fatty liver, etc. are induced.

A combination of increased energy expenditure through exercise and medication of drugs with few side effects is recommended as the safest and most effective method for treating obesity. However, for drugs for treating obesity, severe side effects such as steatorrhea, abdominal pain, vomiting, itching, liver injury, headache, lack of appetite, insomnia, constipation, etc. are reported and definitively reliable safety is not ensured. Therefore, the development of a substance which exhibits superior antiobesity effect in the human body with 100% ensured safety is necessary. For example, Korean Patent Publication No. 10-2015-0105563 discloses a composition for preventing and treating obesity, which contains an herbal extract. However, the development of a substance effective for treatment of obesity through research of fat oxidation/degradation mechanism, energy metabolism-enhancing mechanism, etc. in the body is still insufficient.

DISCLOSURE

Technical Problem

The present disclosure is directed to providing a composition which contains a green tea extract containing gallocatechin gallate as an active ingredient and exhibits superior effect of reducing body fat, and a method for preparing the same.

Technical Solution

The present disclosure provides a composition for reducing body fat, which contains a green tea extract containing 4 wt % or more of gallocatechin gallate based on the total weight of the extract as an active ingredient, and a method for preparing the same.

Advantageous Effects

The composition according to the present disclosure provides a superior effect of reducing body fat as a green tea extract containing 4 wt % or more of gallocatechin gallate is contained as an active ingredient. Accordingly, it can provide substances effective for treating obesity through various researches.

BEST MODE

Figure 1:
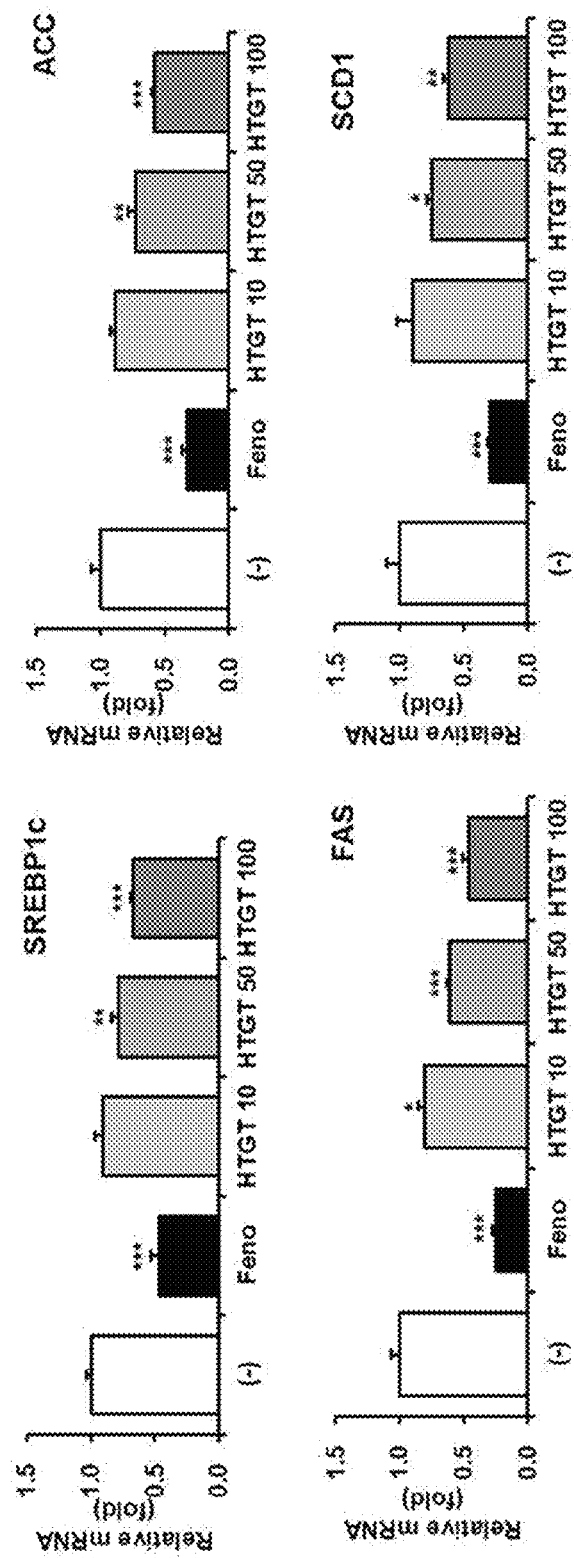
FIGS. 1 and 2 show a result of evaluating the lipid synthesis gene expression-inhibiting effect of a green tea extract.

As the terms used in the present specification, general terms which are currently widely used are adopted as much as possible in consideration of functions in the present disclosure. But, the terms may be changed depending on the intention of those skilled in the art, precedents, the emergence of new technology, etc. Further, in a specific case, a term arbitrarily selected by the applicant may be used and, in that case, the meaning of the term will be described in detail in the corresponding part. Accordingly, the terms used in the present disclosure should be defined based on not the name of the term but the meaning of the term and the contents throughout the present disclosure.

Unless defined otherwise, all the terms used herein, including technical or scientific terms, should have the same meanings as commonly understood by those having ordinary knowledge in the art to which the present disclosure belongs. The commonly understood terms should be interpreted as having the meaning consistent with the meaning in the context of the related art, and should not be interpreted as being ideally or excessively formal unless they are defined clearly in the present disclosure.

A numerical range includes the numerical values defined in the present disclosure. Throughout the present specification, any maximum numerical limitation includes each lower numerical limitation, as if the lower numerical limitation were expressly written herein. Each numerical limitation given throughout the present specification includes each higher numerical limitation, as if the higher numerical limitation were expressly written herein. Each numerical limitation given throughout the present specification includes each narrower numerical range falling within a broader range, as if the narrower numerical range were expressly written herein.

Hereinafter, the present disclosure is described specifically referring to examples and drawings. However, it is obvious that the present disclosure is not limited by the examples and drawings.

In an aspect, the present disclosure provides a composition for reducing body fat, which contains a green tea extract containing gallocatechin gallate (GCG) as an active ingredient.

In an aspect, the present disclosure provides a method for reducing body fat, comprising administering a composition comprising a green tea extract comprising gallocatechin gallate (GCG) as an active ingredient.

The "green tea extract" includes an extract obtained from tea (*Camellia sinensis*), which is an evergreen shrub in the family Theaceae, an extract obtained from tea leaf, etc. which has been fermented by inoculated with *Bacillus subtilis* spp., and a fraction obtained by fractionating the extract with a specific solvent, regardless of extraction method, extraction solvent or the type of the extract. The tea includes one or more selected from a group consisting of the leaf, flower, stem, fruit and root heartwood, specifically leaf, of tea tree. Specifically, the extract may be in the form of powder. The extraction or fractionation may be performed using water, an organic solvent or a mixture thereof. The organic solvent may be an alcohol such as isopropanol, acetone, hexane, ethyl acetate, carbon dioxide or a mixture of two or more of them, although not being limited thereto. The extraction or fractionation may be performed at room temperature or elevated temperature under a condition where the active ingredients of green tea are not destroyed or the destruction is minimized. The alcohol may be a $C_1$-$C_5$ lower alcohol. The number or method of the extraction or fractionation is not specially limited. For example, such methods as cold extraction, ultrasonic extraction, reflux condensation extraction, hot water extraction, etc. may be used. Specifically, after extracting or fractionating the active ingredients at low temperature or elevated temperature, followed by filtering, the filtrate may be concentrated under reduced pressure to obtain the green tea extract of the present disclosure.

The green tea contains polyphenol compounds (flavanols, flavandiols flavonoids and phenolic acids), and most of the polyphenol compounds are flavonols known as "catechin" compounds. In addition, green tea contains pigments, 28 kinds of amino acids including theanine and glutamic acid, minerals, various enzymes, organic acids, carbohydrates, etc. The "catechin" compounds include the following major compounds: catechin (C), epicatechin (EC), gallocatechin (GC), epigallocatechin (EGC), catechin gallate (CG), epicatechin gallate (ECG), gallocatechin gallate (GCG) and epigallocatechin gallate (EGCG). More specifically, they may include (−)-catechin, (−)-epicatechin, (−)-gallocatechin, (−)-epigallocatechin, (−)-catechin gallate, (−)-epicatechin gallate, (−)-gallocatechin gallate and (−)-epigallocatechin gallate.

The "gallocatechin gallate (GCG)" is an epimer of epigallocatechin gallate. As a result of consistent researches for finding out a composition for reducing body fat, the inventors of the present disclosure have surprisingly found out that the activity of reducing body fat is achieved when the content of gallocatechin gallate, the weight ratio of epigallocatechin gallate and gallocatechin gallate and the total catechin content in the extract are within specific ranges, and have completed the present disclosure.

The "total catechin content" means the total content of the 8 catechin compounds, i.e., catechin, epicatechin, gallocatechin, epigallocatechin, catechin gallate, epicatechin gallate, gallocatechin gallate and epigallocatechin gallate.

The "active ingredient" refers to an ingredient which exhibit a desired activity independently or when used together with an inert carrier.

The expression "containing as an active ingredient" may mean being contained as an ingredient which exhibits the effect of reducing body fat or preventing, alleviating or treating obesity.

The effect of "reducing body fat" means the effect of lowering body fat percentage by reducing body fat or the effect of preventing the increase of body fat percentage by preventing the increase of body fat, even without the change in body weight. While the composition for reducing body fat of the present disclosure is being administered or ingested, the effect of reducing body fat may be further increased through regular light exercises. The present disclosure also provides an effect of preventing obesity by preventing the increase of body fat through administration or ingestion of the composition for reducing body fat. By reducing excess body fat, the diseases known to be caused by obesity or overweight, e.g., diabetes, arteriosclerosis, hypertension, cancer, hyperlipidemia, rheumatism, hyperuricemia, degenerative arthritis, gout, stroke, ischemic heart disease, breathing disorder, pancreatitis, nephritis, cataract, Alzheimer's disease, allergic diseases, aging, hyperhidrosis, ischemic disease, and complications of diabetes such as nephrosis, nerve injury or retinal disorder may be treated, alleviated or prevented. For nerve injury, the present disclosure is effective in treating, alleviating or preventing sudden sensorineural hearing loss, disorder (paralysis or pain) of eyes or face, orthostatic hypotension, sweating abnormality, diarrhea or constipation (gastrointestinal symptoms), urination disorder, limb pain, paresthesia and muscle atrophy. For the disorder of eyes, it is effective for cataract, simple retinopathy, pre-proliferative retinopathy and proliferative retinopathy. In addition, for ischemic disease, it is effective for preventing, alleviating or treating cerebral infarction and myocardial infarction.

In an exemplary embodiment of the present disclosure, the green tea extract contains 4 wt % or more gallocatechin gallate based on the total weight of the extract. More specifically, the content may be 4 wt % or more, 4.5 wt % or more, 5 wt % or more, 5.3 wt % or more, 5.5 wt % or more, 5.59 wt % or more or 5.6 wt % or more, although not being limited thereto. The upper limit of the content of gallocatechin gallate is not specially limited.

In an exemplary embodiment of the present disclosure, the green tea extract contains 4-15 wt % of gallocatechin gallate based on the total weight of the extract. More specifically, the content may be 4 wt % or more, 4.5 wt % or more, 5 wt % or more, 5.5 wt % or more or 5.6 wt % or more, and 15 wt % or less, 14.5 wt % or less, 14 wt % or less, 13.5 wt % or less, 13 wt % or less, 12.5 wt % or less, 12 wt % or less, 11.5 wt % or less, 11 wt % or less, 10.5 wt % or less, 10 wt % or less, 9.5 wt % or less, 9 wt % or less, 8.5 wt % or less, 8 wt % or less, 7.5 wt % or less, 7 wt % or less, 6.5 wt % or less, 6 wt % or less or 5.6 wt % or less, although not being limited thereto.

In an exemplary embodiment of the present disclosure, the green tea extract contains 4-15 wt % of epigallocatechin gallate (EGCG) based on the total weight of the extract. More specifically, the content may be 4 wt % or more, 4.5 wt % or more, 5 wt % or more or 5.3 wt % or more, and 15 wt % or less, 14.5 wt % or less, 14 wt % or less, 13.5 wt % or less, 13 wt % or less, 12.5 wt % or less, 12 wt % or less, 11.5 wt % or less, 11 wt % or less, 10.5 wt % or less, 10 wt % or less, 9.5 wt % or less, 9 wt % or less, 8.5 wt % or less, 8 wt % or less, 7.5 wt % or less, 7 wt % or less, 6.5 wt % or less, 6 wt % or less, 5.5 wt % or less or 5.3 wt % or less, although not being limited thereto.

In an exemplary embodiment of the present disclosure, the daily application amount of the green tea extract may be 10-2000 mg/kg. More specifically, the daily application amount may be 10 mg/kg or more, 20 mg/kg or more, 25 mg/kg or more, 50 mg/kg or more, 75 mg/kg or more, 100 mg/kg or more, 125 mg/kg or more, 150 mg/kg or more, 175 mg/kg or more, 200 mg/kg or more, 225 mg/kg or more, 250 mg/kg or more, 275 mg/kg or more, 300 mg/kg or more, 325 mg/kg or more, 350 mg/kg or more, 375 mg/kg or more, or 400 mg/kg or more; and 2000 mg/kg or less, 1750 mg/kg or less, 1500 mg/kg or less, 1250 mg/kg or less, 1000 mg/kg or less, 975 mg/kg or less, 950 mg/kg or less, 925 mg/kg or less, 900 mg/kg or less, 875 mg/kg or less, 850 mg/kg or less, 825 mg/kg or less, 800 mg/kg or less, 775 mg/kg or less, 750 mg/kg or less, 725 mg/kg or less, 700 mg/kg or less, 675 mg/kg or less, 650 mg/kg or less, 625 mg/kg or less, 600 mg/kg or less, 575 mg/kg or less, 550 mg/kg or less, 525 mg/kg or less, 500 mg/kg or less, 475 mg/kg or less, 450 mg/kg or less, 425 mg/kg or less or 400 mg/kg or less, although not being limited thereto. The application may be made once to several times a day. For example, the application may be made 2-24 times a day, 1-2 times in 3 days, 1-6 times a week, 1-10 times in 2 weeks, 1-15 times in 3 weeks, 1-3 times in 4 weeks, or 1-12 times a year.

The "application" refers to the provision of the composition to a subject by any suitable method, and includes administration, coating, absorption, intake, etc. The subject refers to any animal to which the composition can be applied, such as human, monkey, dog, goat, pig, rat, etc.

In an exemplary embodiment of the present disclosure, the green tea extract of the present disclosure may be contained at a content of 0.4-100 wt % based on the total weight of the composition. More specifically, the content may be 0.4 wt % or more, 0.5 wt %, 1 wt % or more, 10 wt % or more, 20 wt % or more, 30 wt % or more, 40 wt % or more, 50 wt % or more, 60 wt % or more, 70 wt % or more, 80 wt % or more or 90 wt % or more; and 100 wt % or less, 90 wt % or less, 80 wt % or less, 70 wt % or less, 60 wt % or less, 50 wt % or less, 40 wt % or less, 30 wt % or less or 20 wt % or less, although not being limited thereto.

The content of the green tea extract may vary depending on formulation, use, number of application and route of application. In particular, when the composition of the present disclosure is prepared into a parenteral formulation such as an injection, etc. or an oral formulation such as a food, a pill, a syrup, etc., the content of the active ingredient of the present disclosure may vary depending on the absorption rate, digestion rate, etc. of the composition. When considering the daily application amount of the composition of the present disclosure, 600-120,000 mg may be applied to a subject weighing 60 kg. Assuming that the daily application amount is 150 g, the content of the green tea extract of the present disclosure may be 0.4-80 wt % based on the total weight of the composition.

In an exemplary embodiment of the present disclosure, the green tea extract contains epigallocatechin gallate (EGCG) and gallocatechin gallate (GCG) at a weight ratio of 1:0.33-3. More specifically, the weight ratio may be 1:0.33 or higher, 1:0.35 or higher, 1:0.4 or higher, 1:0.45 or higher, 1:0.5 or higher, 1:0.55 or higher, 1:0.6 or higher, 1:0.65 or higher, 1:0.7 or higher, 1:0.75 or higher, 1:0.8 or higher, 1:0.9 or higher, 1:1 or higher, 1:1.05 or higher, 1:1.051 or higher, 1:1.052 or higher, 1:1.053 or higher, 1:1.054 or higher, 1:1.055 or higher, 1:1.056 or higher or 1:1.057 or higher; and 1:3 or lower, 1:2.5 or lower, 1:2 or lower, 1:1.5 or lower, 1:1.4 or lower, 1:1.3 or lower, 1:1.2 or lower, 1:1.1 or lower, 1:1.09 or lower, 1:1.08 or lower, 1:1.07 or lower, 1:1.06 or lower, 1:1.059 or lower, 1:1.058 or lower or 1:1.057 or lower, although not being limited thereto.

In an exemplary embodiment of the present disclosure, the green tea extract contains 19-30 wt % of catechin (C), epicatechin (EC), gallocatechin (GC), epigallocatechin (EGC), catechin gallate (CG), epicatechin gallate (ECG), gallocatechin gallate (GCG) and epigallocatechin gallate (EGCG) based on the total weight of the extract. The content of the 8 catechin compounds, or the "total catechin content", may be more specifically, 19 wt % or more, 19.5 wt % or more, 20 wt % or more, 20.5 wt % or more, 21 wt % or more, 21.5 wt % or more, 22 wt % or more, or 24.6 wt % or more, and 30 wt % or less, 29.5 wt % or less, 29 wt % or less, 28.5 wt % or less, 28 wt % or less, 27.5 wt % or less, 27 wt % or less, 26.5 wt % or less, 26 wt % or less, 25.5 wt % or less, 25 wt % or less, 24.5 wt % or less, 24 wt % or less, 23.5 wt % or less, 23 wt % or less, 22.5 wt % or less or 24.6 wt % or less, although not being limited thereto.

In an exemplary embodiment of the present disclosure, the composition is a composition for facilitating the degradation of triglycerides in adipocytes. The accumulated fat may be degraded as the triglyceride is degraded into a glycerol and a free fatty acid.

In an exemplary embodiment of the present disclosure, the active ingredient increases the expression of one or more fatty acid oxidation gene selected from a group consisting of PGC-1α (peroxisome proliferator-activated receptor gamma coactivator 1-alpha), ACO (acyl-CoA oxidase), CPT1 (carnitine palmitoyl transferase 1) and mCAD (medium-chain acyl-CoA dehydrogenase).

In an exemplary embodiment of the present disclosure, the composition reduces the size of adipocytes. The "size of adipocytes" refers to the diameter of adipocytes. Because the size of adipocytes is determined by the amount of fat accumulated in the cells, the reduction of the size of adipocytes may mean that the amount of fat in the cells is decreased.

In an exemplary embodiment of the present disclosure, the composition is a composition for inhibiting the synthesis or accumulation of triglycerides (TGs) in adipocytes. In the body, excess energy is stored mainly in the form of triglycerides. As a first step of reducing body fat, it is necessary to inhibit the synthesis or accumulation of triglycerides.

In an exemplary embodiment of the present disclosure, the composition may inhibit the synthesis or accumulation of triglycerides in adipocytes by inhibiting the expression of lipid synthesis genes. For example, the lipids may be triglycerides. The lipid synthesis genes may be, for example, SREBP1c (sterol regulatory element binding protein 1c), ACC (acetyl-CoA carboxylase), FAS (fatty acid synthase) and stearoyl-CoA desaturase-1 (SCD-1), although not being limited thereto. In an exemplary embodiment of the present disclosure, the active ingredient inhibits the expression of one or more lipid synthesis gene selected from a group consisting of SREBP1c, ACC, FAS and SCD-1.

In an exemplary embodiment of the present disclosure, the composition is a composition for facilitating the activation of mitochondria in adipocytes. In case of obesity, even when fat is degraded in adipocytes, unless the degradation products such as free fatty acids, etc. are consumed adequately through energy metabolism, they may be transported to other cells or tissues, leading to fat accumulation there. This lipid dysregulation may cause metabolic diseases. Because the effect of reducing body fat can be achieved when the fat degraded in the adipocytes should be consumed and converted to ATP, energy metabolism should be activated through mitochondrial activation. That is to say, the optimum effect of reducing body fat can be achieved only when the facilitated degradation of triglycerides and mitochondrial activation in adipocytes are combined.

In an exemplary embodiment of the present disclosure, the composition is a composition for increasing basal metabolic rate. The composition of the present disclosure, which contains the above-described active ingredient, has an effect of increasing the expression of fatty acid oxidation genes, increasing basal metabolic rate by facilitating mitochondrial activation in adipocytes, inhibiting muscle damage, enhancing endurance, strengthening muscle power, preventing muscular pain, etc.

In an exemplary embodiment of the present disclosure, the composition induces the conversion of white adipocytes to beige adipocytes.

Adipocytes are the cells that primarily compose adipose tissue and they are classified into white adipocytes, brown adipocytes and beige (brite) adipocytes depending on cellular functions and morphologies and the origin of differentiation.

The "white adipocytes" are the adipocytes that store fat. They are the cause of adult diseases such as diabetes, obesity, etc. The white adipocytes store energy as triglycerides (TGs) and use free fatty acids when energy is necessary. The release of free fatty acids requires degradation (hydrolysis) of triglycerides (TGs), which is regulated primarily by the activation of cAMP-dependent protein kinase A of cytosolic lipases including adipose triglyceride lipase (ATGL) and hormone-sensitive lipase (HSL).

The "brown adipocytes" and "beige (brite) adipocytes" are the adipocytes that burn fat. In the brown adipocytes, uncoupling of protons is induced in ATP synthesis, which moves down their mitochondrial gradient, is induced, leading to non-shivering thermogenesis. Accordingly, the brown adipocytes and the beige adipocytes play an important role in body temperature regulation and energy production.

The brown adipocytes and the beige adipocytes have several differences. The brown adipocytes are differentiated from precursor cells (Myf5+/Pax7+ precursors) such as muscle cells and are found mainly in the scapula, collarbone, kidney, etc. In mouse, they are differentiated just before birth and maintain their functions and morphologies throughout lifetime. But, in human, it is known that they occur temporarily in the youth and disappear gradually in the adulthood. The beige adipocytes are differentiated from white adipocytes (trans-differentiation) or from white adipose precursor cells (PDGFRα+/SCA1+ precursors) (de novo differentiation), and occur as specific white adipose tissue (mainly hypodermis) when exposed to cold environments.

If white adipocytes are converted to brown adipocytes, the amount of burnt fat is increased as compared to the fat stored in the body. As a result, it becomes easier to maintain body weight and alleviate obesity even when food of the same calorie is taken. But, the composition of the present disclosure induces the conversion of white adipocytes to beige adipocytes rather than to brown adipocytes. The composition induces the conversion of white adipocytes to beige adipocytes, or so-called beige adipocyte transformation.

In an exemplary embodiment of the present disclosure, the composition increases the expression of UCP1 (uncoupling protein 1) in adipocyte. UCP1 is present in the mitochondrial inner membrane of brown adipocytes and serves to uncouple oxidation and phosphorylation. UCP1 is used as a molecular marker of brown adipocytes because it is not expressed in other cells including white adipocytes. UCP1 blocks the pathway from photophosphorylation to ATP synthesis, and the energy is dissipated as heat.

In an exemplary embodiment of the present disclosure, the composition is a pharmaceutical composition for preventing, alleviating or treating obesity.

The "obesity" refers to a condition in which excess body fat is accumulated in the body. Obesity is diagnosed when whose body fat weight is 25% or higher based on body weight, for men, and 30% or higher for women. Obesity is caused when calorie intake from food exceeds calorie expenditure through exercise. Obesity leads to stout appearance and is often accompanied by such symptoms as shortness of breath, joint pain, diabetes, hypertension, etc.

The "pharmaceutical composition" refers to a composition which is suitable to be administered to a subject in need of prevention, alleviation or treatment of a disease.

The "subject" refs to a subject in need of prevention, alleviation or treatment of a disease, more specifically mammals such as human or non-human primates, mouse, rat, dog, cat, horse, cattle, etc.

The "prevention" refers to any action of inhibiting or delaying obesity by administering the composition of the present disclosure. The "alleviation" refers to any action of improving or favorably changing obesity by administering the composition. The "treatment" refers to any action of improving or favorably changing symptoms in a subject suspected of or having obesity by administering the composition of the present disclosure.

When the active ingredient of the present disclosure is contained in a pharmaceutical composition, it may further contain, in addition to the active ingredient of the present disclosure, a pharmaceutically acceptable carrier, i.e., one or more of saline, sterile water, Ringer's solution, buffered saline, cyclodextrin, dextrose solution, maltodextrin solution, glycerol, ethanol and liposome. If necessary, other common additives such as an antioxidant, a buffer, etc. may be further contained. In addition, an injectable formulation such as an aqueous solution, a suspension, an emulsion, etc., a pill, a capsule, a granule or a tablet may be prepared by additionally adding a diluent, a dispersant, a surfactant, a binder and/or a lubricant.

The pharmaceutical composition is administered in a pharmaceutically effective amount. The "pharmaceutically effective amount" refers to an amount sufficient to prevent or treat a disease at a reasonable benefit/risk ratio applicable to medical treatment. An effective dose level may be determined depending on various factors including the type and severity of a disease, drug activity, drug sensitivity, administration time, administration route, excretion ratio, treatment period, concurrently used drugs and other pharmaceutically well-known factors.

The pharmaceutical composition may be prepared into an oral formulation (e.g., powder, tablet, capsule, syrup, pill or granule), a parenteral formulation (e.g., injection), a systemic formulation or a topical formulation.

The pharmaceutical composition may be administered as an independent therapeutic agent or in combination with another therapeutic agent. When administered in combination with another therapeutic agent, they may be administered sequentially or simultaneously and may be administered through single or multiple administration. It is important to administer a minimum amount which can provide the maximum effect without side effects in consideration of all the factors described above, which can be easily determined by those skilled in the art. In addition, the pharmaceutical composition may be used either alone or in combination with surgery, radiation therapy, hormone therapy, chemotherapy or therapies using biological response modifiers.

In an exemplary embodiment of the present disclosure, the composition is a food composition for preventing or alleviating obesity.

The "prevention" refers to any action of inhibiting or delaying obesity by administering the composition of the present disclosure. The "alleviation" refers to any action of improving or favorably changing obesity by administering the composition.

The "food" may be mean, sausage, bread, chocolate, candies, snacks, confectionery, pizza, ramen, other noodles, gums, dairy products including ice cream, soups, beverages, tea, drinks, alcoholic beverages, vitamin complexes, functional health foods, health foods, etc., and includes all foods in common meanings.

The functional health food is the same term as food for special health use (FOSHU), and means a food with high medical effect, which is processed to efficiently exhibit a biological regulatory function in addition to nutrition. Here, the function (functional) means obtaining of an effect useful for health care such as regulation of nutrition depending on the structure and function of the human body or physiological action. The health food means a food which has an effect of actively maintaining or enhancing health as compared with general foods, and a health supplement food means a food for health supplement. Sometimes, the terms functional health food, health food and health supplement food are used interchangeably.

The food can be prepared by a method commonly employed in the art, and ingredients and components commonly used in the art may be added for the preparation. In addition, the food can be prepared into any food formulation without limitation. The food composition of the present disclosure may be prepared into various formulations. Because it can be advantageously taken for a long period of time without side effects, unlike general drugs, and has excellent portability, the food composition of the present disclosure can be taken as a supplement for enhancing the effect of preventing or alleviating obesity.

In an exemplary embodiment of the present disclosure, the composition is a feed composition for preventing or alleviating obesity.

The "feed" refers to any natural or artificial diet, meal or the ingredients of the meal that can be eaten, ingested and digested by livestock. The feed may include a feed additive or a feed supplement. The type of the feed is not particularly limited, and any feed commonly used in the art may be used. Non-limiting examples of the feed may include phytogenic feeds such as grains, root vegetables, food processing byproducts, algae, fibers, pharmaceutical byproducts, oils and fats, starches, cucurbits, grain byproducts, etc. and animal feeds such as proteins, inorganic substances, oils and fats, minerals, single-cell proteins, zooplanktons, foods, etc. These feeds may be used alone or in combination.

In an exemplary embodiment of the present disclosure, the green tea extract is obtained by a method including a high-temperature treatment step of treating green tea with steam at 75-100° C. under a pressure of 1-2 $kgf/cm^2$ for 1-7 hours.

In another aspect, the present disclosure provides a method for preparing the composition described above, which includes a high-temperature treatment step of treating green tea with steam at 75-100° C. under a pressure of 1-2 $kgf/cm^2$ for 1-7 hours.

In an exemplary embodiment of the present disclosure, before the high-temperature treatment step, a step of obtaining a first green tea extract by adding one or more of water and a $C_1$-$C_4$ alcohol to green tea and performing extraction at 50-65° C. for 30 minutes to 4 hours and a step of obtaining a first green tea extract by filtering and concentrating the same under reduced pressure. After the extraction and filtration, one or more of water and a $C_1$-$C_4$ alcohol may be removed under reduced pressure.

The $C_1$-$C_4$ alcohol may be ethanol. In another aspect, the alcohol may be 20% or higher, 30% or higher, 40% or higher, 50% or higher, 60% or higher or 70% or higher ethanol. In another aspect, the alcohol may be 70% or lower, 60% or lower, 50% or lower, 40% or lower or 30% or lower ethanol.

In an exemplary embodiment of the present disclosure, the first green tea extract may be obtained by performing extraction at 50° C. or higher, 55° C. or higher, 60° C. or higher, 62° C. or higher or 64° C. or higher, and 65° C. or lower, 62° C. or lower, 60° C. or lower, 55° C. or lower or 52° C. or lower, although not being limited thereto.

In an exemplary embodiment of the present disclosure, the first green tea extract may be obtained by performing extraction for 30 minutes or longer, 40 minutes or longer, 50 minutes or longer, 60 minutes or longer, 70 minutes or longer, 80 minutes or longer, 90 minutes or longer, 100 minutes or longer, 120 minutes or longer, 140 minutes or longer, 160 minutes or longer, 180 minutes or longer, 200 minutes or longer or 220 minutes or longer, and 240 minutes or shorter, 220 minutes or shorter, 200 minutes or shorter, 180 minutes or shorter, 160 minutes or shorter, 140 minutes or shorter, 120 minutes or shorter, 100 minutes or shorter, 90 minutes or shorter, 80 minutes or shorter, 70 minutes or shorter, 60 minutes or shorter, 50 minutes or shorter or 40 minutes or shorter, although not being limited thereto.

In an exemplary embodiment of the present disclosure, the temperature of the steam in the high-temperature treatment step is 75-100° C. More specifically, the temperature may be 75° C. or higher; and 100° C. or lower, 98° C. or lower, 95° C. or lower, 90° C. or lower, 85° C. or lower, 80° C. or lower or 75° C. or lower, although not being limited thereto.

In an exemplary embodiment of the present disclosure, the pressure of the steam in the high-temperature treatment step is 1-2 $kgf/cm^2$. More specifically, the pressure may be 1 $kgf/cm^2$ or higher, 1.2 $kgf/cm^2$ or higher, 1.4 $kgf/cm^2$ or higher or 1.5 $kgf/cm^2$ or higher, and 2 $kgf/cm^2$ or lower, 1.8 $kgf/cm^2$ or lower, 1.7 $kgf/cm^2$ or lower or 1.5 $kgf/cm^2$ or lower.

In an exemplary embodiment of the present disclosure, the high-temperature treatment step may be accompanied by stirring, and the stirring in the high-temperature treatment step may be performed for 1 hour or longer, 2 hours or longer, 3 hours or longer, 4 hours or longer or 5 hours or longer, and 7 hours or shorter, 6 hours or shorter or 5 hours or shorter, although not being limited thereto.

In an exemplary embodiment of the present disclosure, a step of filtration and concentration under reduced pressure may be further included after the high-temperature treatment step.

As another exemplary embodiment, the present disclosure provides a use of a green tea extract containing gallocatechin gallate for preparation of a composition for reducing body fat.

As another exemplary embodiment, the present disclosure provides a method for reducing body fat, which includes a step of administering a composition containing a green tea extract containing gallocatechin gallate as an active ingredient to a subject in need thereof.

As another exemplary embodiment, the present disclosure provides a green tea extract containing gallocatechin gallate for use in reducing body fat.

EXAMPLES

Hereinafter, the present disclosure is described in detail through examples. However, the following examples are merely examples for helping general understanding of the present disclosure, and the present disclosure is not limited by the examples.

<Preparation Example 1> Preparation of Green Tea Extract, Fermented Green Tea Extract and Heat-Transformed Green Tea Extract 1. Preparation of Green Tea Extract (GTE)

After adding 1000 mL of 50% ethanol to 100 g of green tea (Camellia sinensis, Jeju O'Sulloc Farm, Korea), the mixture was refluxed at 60° C. for 1 hour under stirring. After cooling to room temperature and filtering, 23 g of a notified green tea extract (GTE) was obtained as dark brown powder by distilling the obtained solution under reduced pressure (yield: 23%).

2. Preparation of Fermented Green Tea Extract (FGT)

Water was added to 100 g of green tea (Camellia sinensis, Jeju O'Sulloc Farm, Korea) to adjust water content to 40 wt %. Then, after inoculating $5 \times 10^6$ cfu/g of Bacillus Subtilis and performing fermentation at 50° C. for 3 days, fermentation was performed at 80° C. for 4 days. After drying the fermented green tea with hot air of 80° C. to water content of 4-6 wt %, post-fermented green tea was prepared by aging at 10° C. for 100 days. After immersing 1 kg of the post-fermented green tea in 15 L of 50% (v/v) ethanol solution and refluxing at 70° C. for 3 hours, extraction was performed at room temperature for 12 hours. After filtering the extract and concentrating the same under reduced pressure, a fermented green tea extract (FGT) in the form of powder was prepared through freeze-drying. The yield was 15-20%, and the prepared powder was stored at 4° C. until use.

3. Preparation of Heat-Transformed Green Tea Extract (HTGT)

For preparation of a heat-transformed green tea extract, after adding 1000 mL of 50% ethanol to 100 g of green tea (Camellia sinensis, Jeju O'Sulloc Farm, Korea), the mixture was refluxed at 60° C. for 1 hour under stirring and a first green tea extract was obtained by filtering and distilling the same under reduced pressure. After concentrating the first green tea extract, it was stirred for 5 hours with steam of 1.5 kgf/cm$^2$ at 75° C. Then, after cooling to room temperature and filtering insoluble substance, 10 g of a heat-transformed green tea extract (HTGT) was obtained through concentration under reduced pressure. The ingredients of the heat-transformed green tea extracts obtained by stirring for 1-7 hours were analyzed in Test Example 1. The extract obtained by stirring for 5 hours showed the highest conversion from epigallocatechin gallate (EGCG) to gallocatechin gallate (GCG) without decrease in the content of total 8 catechins. Therefore, the stirring time was set to 5 hours.

<Test Example 1> Analysis of Ingredients of Green Tea Extract

1. Analysis Method

The green tea extracts prepared in Preparation Example 1 (green tea extract, fermented green tea extract and heat-transformed green tea extract) were filtered through a 0.45-µm PVDF filter, pretreated and then loaded in an analytic instrument (HPLC). HPLC-grade reagents were used for analysis and data processing was performed using the Waters Empower II program. The analysis condition is described in Table 1.

TABLE 1

| | |
|---|---|
| Column | Thermofisher C18, 5 µm, 4.6 × 250 mm |
| Detector | UV 280 nm |
| Dilution | A: 0.1% TFA (trifluoroacetic acid) in water |
| | B: 5% acetonitrile (ACN) |
| Gradient profile | 0-29 min, A(90):B(10) |
| | 30-41 min, A(85):B(15) |
| | 42-43 min, A(80):B(20) |
| | 44-48 min, A(5):B(95) |
| | 49-50 min, A(90):B(10) |
| Flow rate | 1 mL/min |
| Injection volume | 20 µL |

2. Analysis Result

The analysis result is shown in Table 2. C stand for catechin, EC for epicatechin, GC for gallocatechin, EGC for epigallocatechin, CG for catechin gallate, ECG for epicatechin gallate, GCG for gallocatechin gallate, and EGCG for epigallocatechin gallate. All units are wt % based on the total weight of the green tea extract.

TABLE 2

| | Caffeine | C | EC | GC | EGC | CG | ECG | GCG | EGCG | Epicatechin | Epicatechin epimer | Total catechin |
|---|---|---|---|---|---|---|---|---|---|---|---|---|
| GTE | 3.2 | 0.2 | 3.9 | 0.6 | 13.0 | N.D | 3.4 | 0.3 | 19.0 | 39.3 | 1.1 | 40.4 |
| FGT | 4.3 | N.D | 0.8 | N.D | 1.8 | 0.3 | 1.6 | 3.0 | 5.7 | 9.3 | 3.3 | 13.2 |
| HTGT | 3.9 | 1.6 | 1.0 | 4.9 | 3.6 | 1.3 | 1.3 | 5.6 | 5.3 | 11.2 | 13.4 | 24.6 |

As seen from Table 2, it was confirmed that the composition of the heat-transformed green tea extract (HTGT) was different from those of the green tea extract (GTE) and the fermented green tea extract (FGT). Specifically, the heat-transformed green tea extract (HTGT) showed a lower EGC content (3.6 wt %) as compared to the green tea extract (GTE). In addition, it showed a lower EGCG content (5.3 wt %) and a lower total catechin content (24.6 wt %) than the green tea extract (GTE) and the fermented green tea extract (FGT), and showed three epicatechin epimers not detected in the green tea extract (GTE) or the fermented green tea extract (FGT).

As seen from Table 2, the green tea extract, the fermented green tea extract and the heat-transformed green tea extract showed different total catechin contents (green tea extract 40.4 wt %, fermented green tea extract 13.2 wt %, heat-transformed green tea extract 24.6 wt %) and epicatechin contents (green tea extract 39.3 wt %, fermented green tea extract 9.9 wt %, heat-transformed green tea extract 11.2 wt %), and the ratio of the main active ingredients of the heat-transformed green tea extract, i.e., EGCG and GCG, was also completed different as 19.0:0.3 (green tea extract), 5.7:3.0 (fermented green tea extract) and 5.3:5.6 (heat-transformed green tea extract). Accordingly, it seems reasonable to regard the green tea extract and processed green tea extracts as different substances exhibiting different metabolic efficacy.

<Reference Example 1> Differentiation of Adipocytes

Mouse-derived 3T3-L1 adipocytes (American Type Culture Collection, ATCC) were cultured in an incubator using DMEM (Dulbecco's modified Eagle's medium; Sigma-Aldrich) containing 10% bovine calf serum (BCS; HyClone) and 1% penicillin/streptomycin (P/S; Sigma-Aldrich) under a standard condition (37° C., 5% $CO_2$). For cellular differentiation, 48 hours after the cells were filled 100% on a plate, they were cultured again for 48 hours after replacing the medium with DMEM supplemented with 10% fetal bovine serum (FBS; Hyclone), 1% P/S, 0.5 mM 3-isobutyl-1-methylxanthine (IBMX; Sigma-Aldrich), 1 μM dexamethasone (Sigma-Aldrich) and 5 μg/mL insulin (Sigma-Aldrich). Then, differentiation of adipocytes was induced by culturing the cells additionally for 10 days while replacing the medium with a medium supplemented with 10% FBS, 5 μg/mL insulin and 1% P/S at two-day intervals.

<Reference Example 2> Method for Evaluation of Gene Expression

After extracting RNA using Trizol™ reagent (Thermo Fisher Scientific), cDNA was synthesized using a RevertAid™ 1st strand cDNA synthesis kit (Thermo Fisher Scientific). Then, the expression level of target genes was quantified by CFX96 real-time quantitative PCR (qPCR; Bio-Rad) using a housekeeping gene (cyclophilin).

<Test Example 2> Evaluation of Lipid Synthesis Gene Expression-Inhibiting Effect of Green Tea Extract 1

1. Evaluation Method

The adipocytes differentiated as in Reference Example 1 were treated with the heat-transformed green tea extract (HTGT) prepared in Preparation Example 1 at 10, 50 or 100 μg/mL (HTGT 10, HTGT 50 or HTGT 100) for 24 hours. A control group for comparison was treated with 30 μM fenofibrate (Feno) which inhibits fat synthesis and facilitates fatty acid oxidation. A negative control group was treated with a vehicle (distilled water).

A result of quantifying the expression level of fat synthesis-related genes (SREBP1c, ACC, FAS and SCD-1) according to the method of Reference Example 2 is shown in FIG. 1 (*$P<0.001$ vs. (−), $P<0.01$ vs. (−), *$P<0.05$ vs. (−)).

2. Evaluation Result

As seen from FIG. 1, the treatment with the heat-transformed green tea extract (HTGT) of the present disclosure inhibited the expression of the lipid synthesis genes in a concentration-dependent manner like the Feno-treated control group. Through this, it was confirmed that a composition containing the heat-transformed green tea extract (HTGT) has superior effect of inhibiting lipid synthesis or accumulation.

<Test Example 3> Evaluation of Lipid Synthesis Gene Expression-Inhibiting Effect of Green Tea Extract 2

As shown in Table 2, the total catechin content of the green tea extract (GTE) was 40.4 wt %, and the total catechin content of the heat-transformed green tea extract (HTGT) was 24.6 wt %. Thus, after making correction such that the total catechin content of the green tea extract (GTE) was equal to the total catechin content of the heat-transformed green tea extract (HTGT) (24.6/40.4≈0.61), experiment was conducted as follows.

1. Evaluation Method

The adipocytes differentiated as in Reference Example 1 were treated with the green tea extract (GTE) prepared in Preparation Example 1 at 61 or 100 μg/mL (GTE 61 or GTE 100) for 24 hours, or with the heat-transformed green tea extract (HTGT) at 100 μg/mL (HTGT 100) for 24 hours. A control group for comparison was treated with 30 μM fenofibrate (Feno) which inhibits fat synthesis and facilitates fatty acid oxidation. A negative control group was treated with a vehicle (distilled water).

Figure 2:
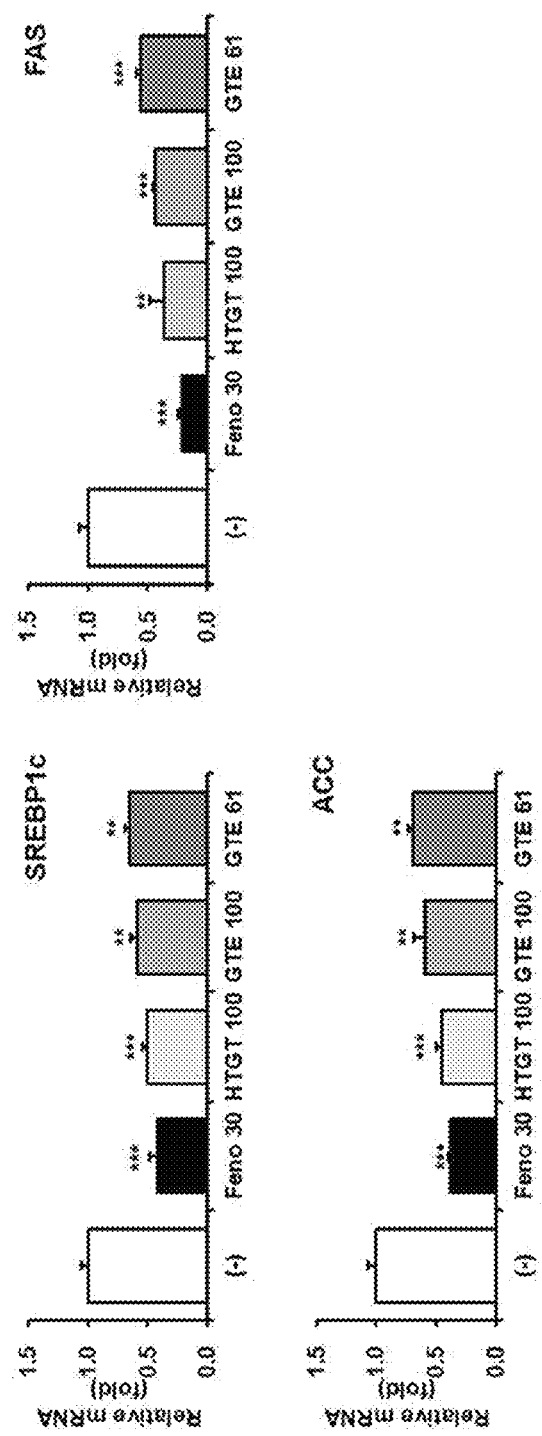

A result of quantifying the expression level of fat synthesis-related genes (SREBP1c, ACC and FAS) according to the method of Reference Example 2 is shown in FIG. 2 (*$P<0.001$ vs. (−), $P<0.01$ vs. (−), *$P<0.05$ vs. (−)).

2. Evaluation Result

As seen from FIG. 2, the treatment with the heat-transformed green tea extract (HTGT) of the present disclosure inhibited the expression of the lipid synthesis genes as compared to the treatment with the green tea extract (GTE). In addition, when correction was made such that the total catechin content of the green tea extract (GTE) was equal to the total catechin content of the heat-transformed green tea extract (HTGT), the treatment with the heat-transformed green tea extract (HTGT) of the present disclosure showed better effect of inhibiting the expression of the lipid synthesis genes as compared to the treatment with the green tea extract (GTE).

<Test Example 4> Evaluation of Lipid Synthesis or Accumulation-Inhibiting Effect of Green Tea Extract 1. Evaluation Method In order to investigate the effect of the inhibited expression of the lipid synthesis-related genes by the heat-transformed green tea extract (HTGT) on fat synthesis and accumulation, the adipocytes differentiated as in Reference Example 1 were treated with the heat-transformed green tea extract (HTGT) prepared in Preparation Example 1 at 10, 50 or 100 μg/mL (HTGT 10, HTGT 50 or HTGT 100) for 24 hours. A control group for comparison was treated with 30 μM fenofibrate (Feno) which inhibits fat synthesis and facilitates fatty acid oxidation. A negative control group was treated with a vehicle (distilled water).

Then, the cells were washed twice with phosphate-buffered saline (PBS; Sigma-Aldrich) and then fixed in formalin solution (Sigma-Aldrich). 15 minutes later, after washing twice with PBS again, the triglycerides accumulated in the cells were stained using 300 nM Nile red solution (Sigma-Aldrich). 30 minutes later, after washing 3 times with PBS again, the cells were observed with a fluorescence microscope. The images and quantification result of the lipids are shown in FIG. 3.

2. Evaluation Result

Figure 3:
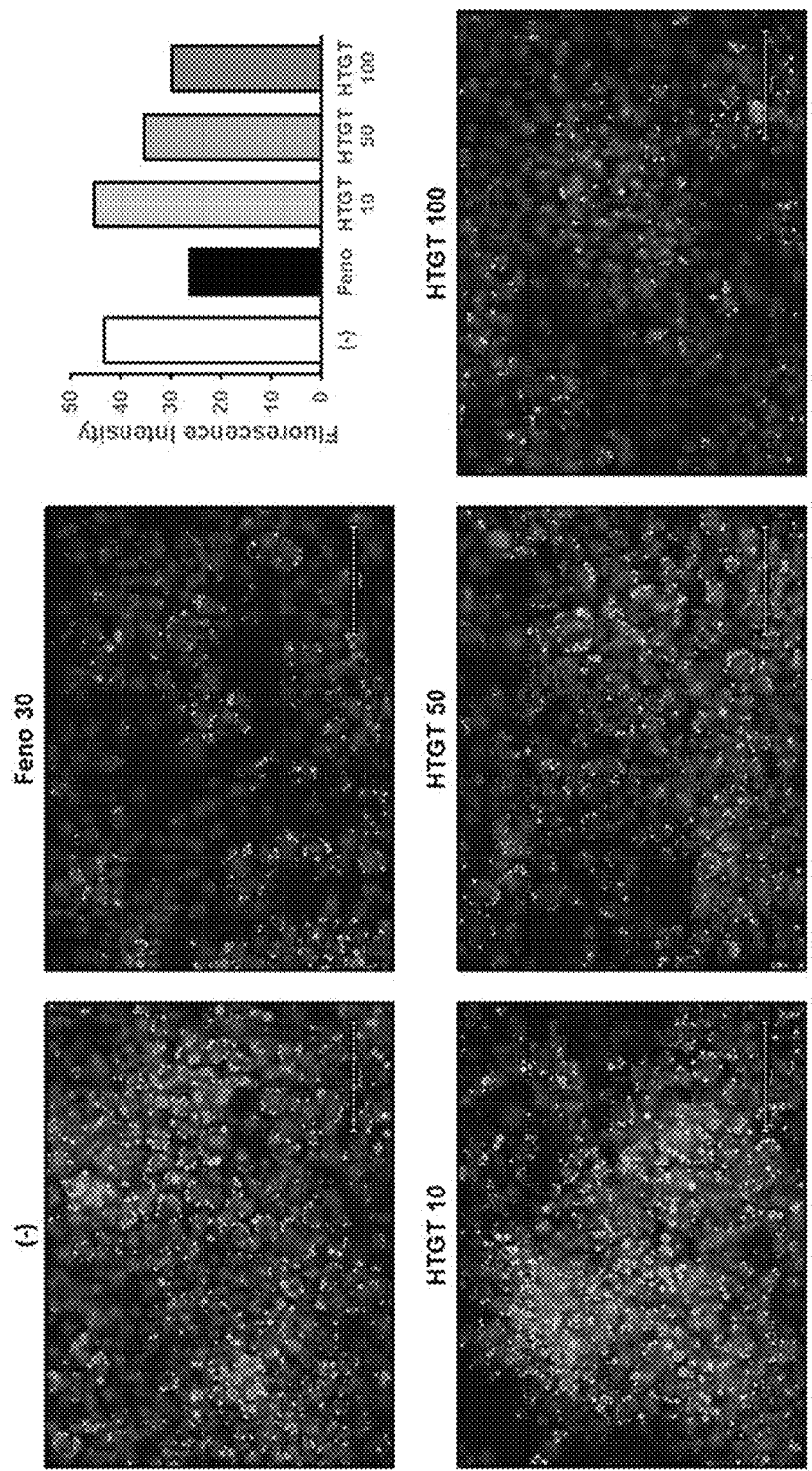
FIG. 3 shows a result of evaluating the lipid synthesis or accumulation-inhibiting effect of a green tea extract.

As seen from FIG. 3, it was confirmed that the heat-transformed green tea extract (HTGT) of the present disclosure has an effect of inhibiting the synthesis or accumulation of lipids in adipocytes in a concentration-dependent manner.

<Test Example 5> Lipid Synthesis or Accumulation-Inhibiting Effect of Ingredients of Green Tea Extract Experiment was performed as follows to compare the effect of inhibiting lipid synthesis or accumulation depending on the ratio of the contents of gallocatechin gallate (GCG) and epigallocatechin gallate (EGCG) in the green tea extract.

1. Evaluation Method

The adipocytes differentiated as in Reference Example 1 were treated with epigallocatechin gallate (EGCG) and gallocatechin gallate (GCG) at 10:0 to 0:10 (10:0, 8:2, 6:4, 5:5, 4:6, 2:8, 0:10) base on weight for 24 hours. A negative control group was treated with a vehicle (distilled water).

Then, the cells were washed twice with phosphate-buffered saline (PBS; Sigma-Aldrich) and then fixed with formalin solution (Sigma-Aldrich). 15 minutes later, after washing twice with PBS again, the triglycerides accumulated in the cells were stained using 300 nM Nile red solution (Sigma-Aldrich). 30 minutes later after washing 3 times with PBS again, the cells were observed with a fluorescence microscope. The result of quantifying the amount of lipids is shown in FIG. 4 (*$P<0.001$ vs. (−), $P<0.01$ vs. (−), &&&$P<0.001$ vs. GCG 100% (0:10), &&$P<0.01$ vs. GCG 100% (0:10), &$P<0.05$ vs. GCG 100% (0:10)).

2. Evaluation Result

Figure 4:
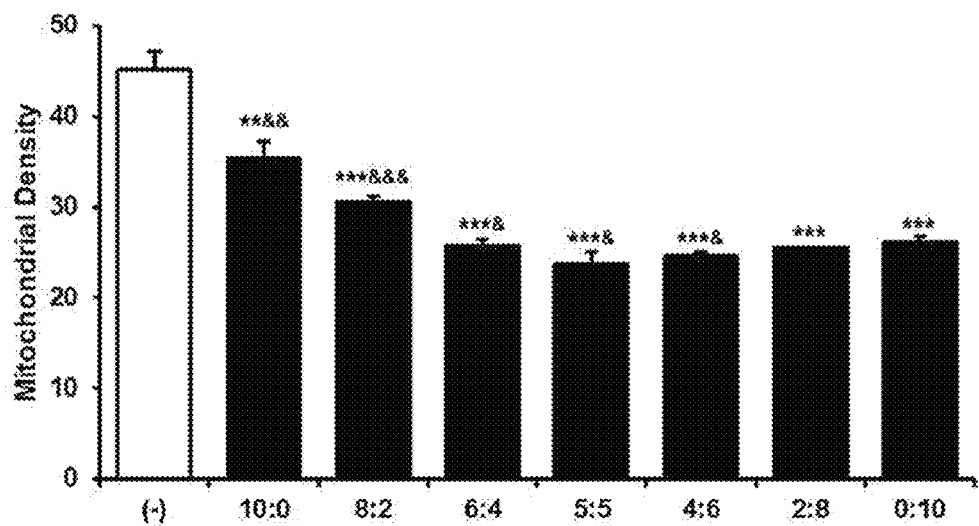
FIG. 4 shows a result of evaluating the lipid synthesis or accumulation-inhibiting effect of the ingredients of a green tea extract.

As seen from FIG. 4, the heat-transformed green tea extract (HTGT) of the present disclosure showed superior effect of inhibiting lipid synthesis or accumulation when the ratio of the contents of gallocatechin gallate (GCG) and epigallocatechin gallate (EGCG) was between 6:4 and 4:6.

<Test Example 6> Evaluation of Fatty Acid Oxidation Gene Expression-Increasing Effect of Green Tea Extract 1

Experiment was performed as follows to identify the effect of increasing the expression of fatty acid oxidation genes depending on the concentration of the heat-transformed green tea extract (HTGT) of the present disclosure.

1. Evaluation Method

The adipocytes differentiated as in Reference Example 1 were treated with the heat-transformed green tea extract (HTGT) prepared in Preparation Example 1 at 10, 50 or 100 μg/mL (HTGT 10, HTGT 50 or HTGT 100) for 24 hours. A control group for comparison was treated with 30 μM fenofibrate (Feno) which inhibits fat synthesis and facilitates fatty acid oxidation. A negative control group was treated with a vehicle (distilled water).

After extracting RNA using Trizol™ reagent (Thermo Fisher Scientific), cDNA was synthesized using a RevertAid™ 1st strand cDNA synthesis kit (Thermo Fisher Scientific). Then, the expression level of fatty acid oxidation-associated genes (ACO, CPT1 and mCAD) was quantified by CFX96 real-time quantitative PCR (qPCR; Bio-Rad) using a housekeeping gene (cyclophilin). The result is shown in FIG. 5 (*$P<0.001$ vs. (−), $P<0.01$ vs. (−), *$P<0.05$ vs. (−)).

2. Evaluation Result

Figure 5:
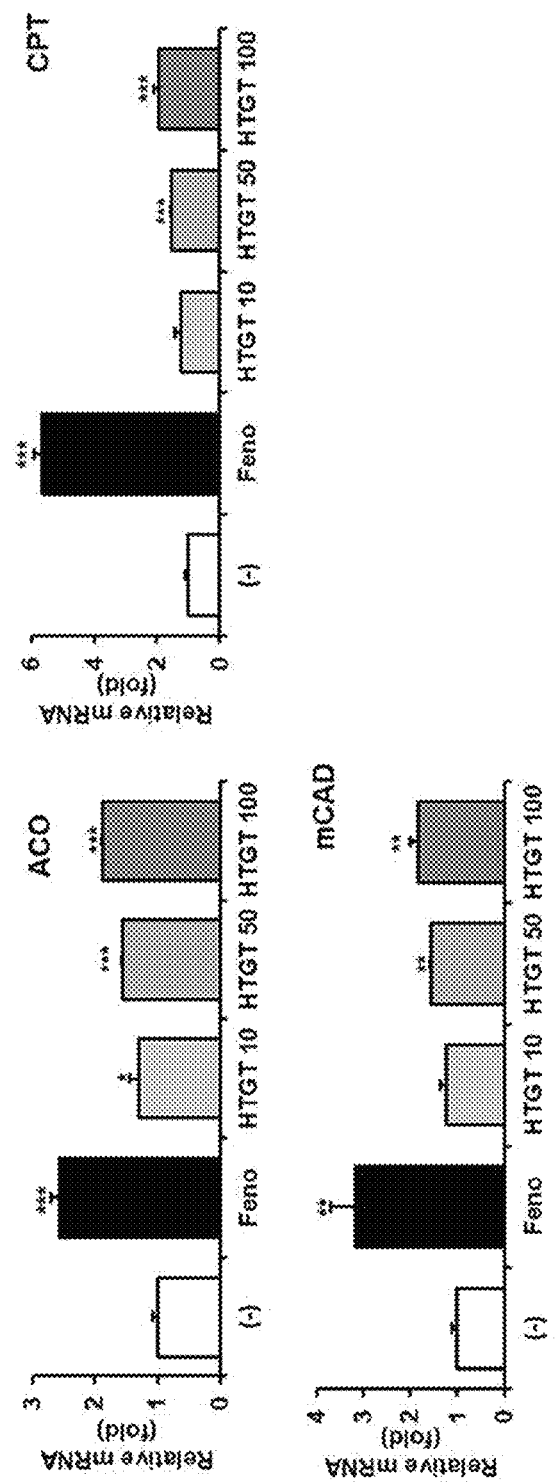
FIGS. 5, 6 and 8 show a result of evaluating the fatty acid oxidation gene expression-increasing effect of a green tea extract.

As seen from FIG. 5, the treatment with the heat-transformed green tea extract (HTGT) of the present disclosure increased the expression of the fatty acid oxidation genes in a concentration-dependent manner as in the Feno-treated control group. From this, it can be expected that a composition containing the heat-transformed green tea extract (HTGT) has superior fatty acid-oxidizing effect.

<Test Example 7> Evaluation of Fatty Acid Oxidation Gene Expression-Increasing Effect of Green Tea Extract 2

Experiment was performed as follows to compare the fatty acid oxidation gene expression-increasing effect of the heat-transformed green tea extract (HTGT) of the present disclosure, the green tea extract (GTE) and the fermented green tea extract (FGT).

1. Evaluation Method

The adipocytes differentiated as in Reference Example 1 were treated with the green tea extract (GTE) prepared in Preparation Example 1, the fermented green tea extract (FGT) or the heat-transformed green tea extract (HTGT) at 100 μg/mL (GTE 100, FGT 100 or HTGT 100) for 24 hours. A control group for comparison was treated with 100 μM fenofibrate (Feno) which inhibits fat synthesis and facilitates fatty acid oxidation. A negative control group was treated with a vehicle (distilled water).

Figure 6:
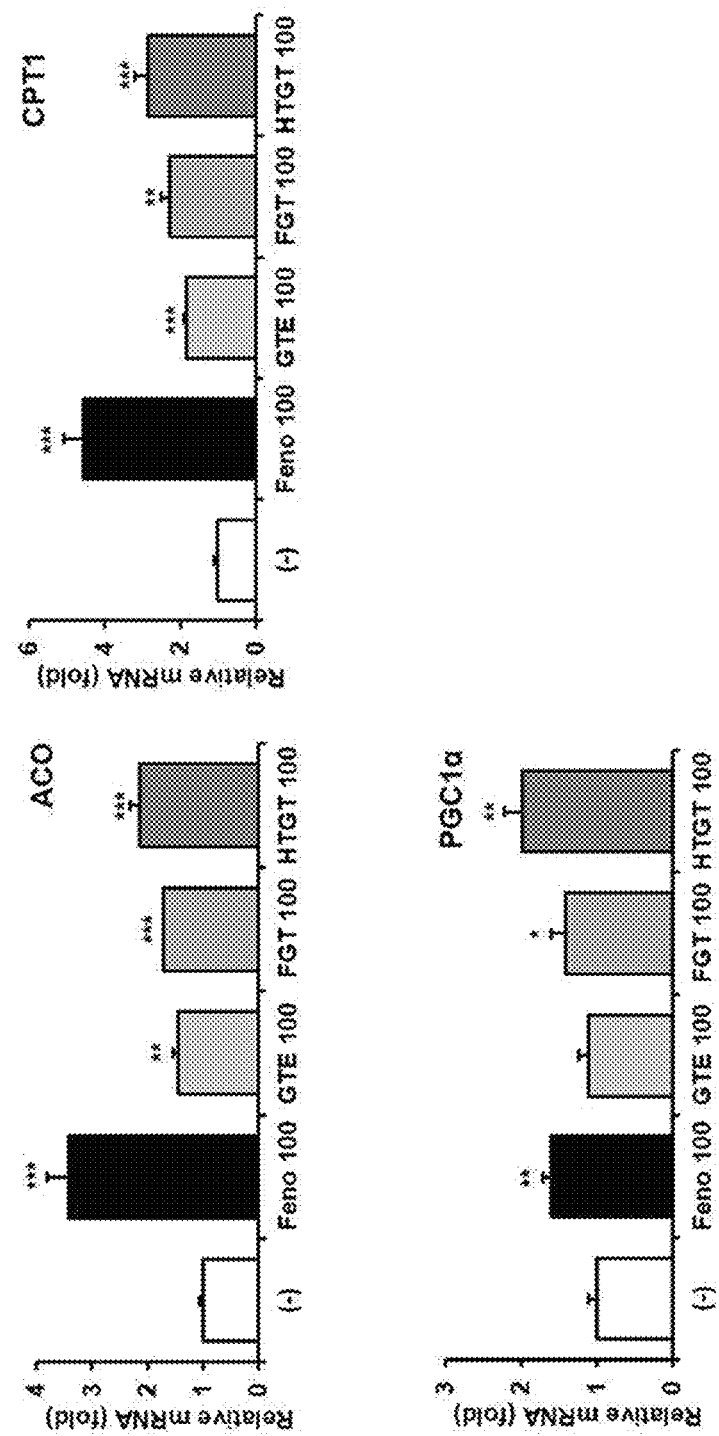

The result of quantifying the expression level of fatty acid oxidation-associated genes (PGC-1α, ACO and CPT1) according to the method of Reference Example 2 is shown in FIG. 6 (*$P<0.001$ vs. (−), $P<0.01$ vs. (−), *$P<0.05$ vs. (−)).

2. Evaluation Result

As seen from FIG. 6, the treatment with the heat-transformed green tea extract (HTGT) of the present disclosure increased the expression of the fatty acid oxidation genes as compared to the treatment with the green tea extract (GTE) or the fermented green tea extract (FGT). From this, it can be seen that a composition containing the heat-transformed green tea extract (HTGT) has superior fatty acid-oxidizing effect.

<Test Example 8> Evaluation of Fatty Acid Oxidation Gene Expression-Increasing Effect of Ingredients of Green Tea Extract 3

Experiment was performed as follows to compare the fatty acid oxidation gene expression-increasing effect depending on the contents and ratio of gallocatechin gallate (GCG) and epigallocatechin gallate (EGCG), which are ingredients of green tea extract.

1. Evaluation Method

The adipocytes differentiated as in Reference Example 1 were treated with the green tea extract (GTE), the fermented green tea extract (FGT) or the heat-transformed green tea extract (HTGT), containing gallocatechin gallate (GCG) and epigallocatechin gallate (EGCG) as described in Table 2, for 24 hours (GTE: GCG 0.3 wt %, EGCG 19.0 wt %; FGT: GCG 3.0 wt %, EGCG 5.7 wt %; HTGT: GCG 5.6 wt %, EGCG 5.3 wt %). A control group for comparison was treated with 100 μM fenofibrate (Feno) which inhibits fat synthesis and facilitates fatty acid oxidation. A negative control group was treated with a vehicle (distilled water).

Figure 7:
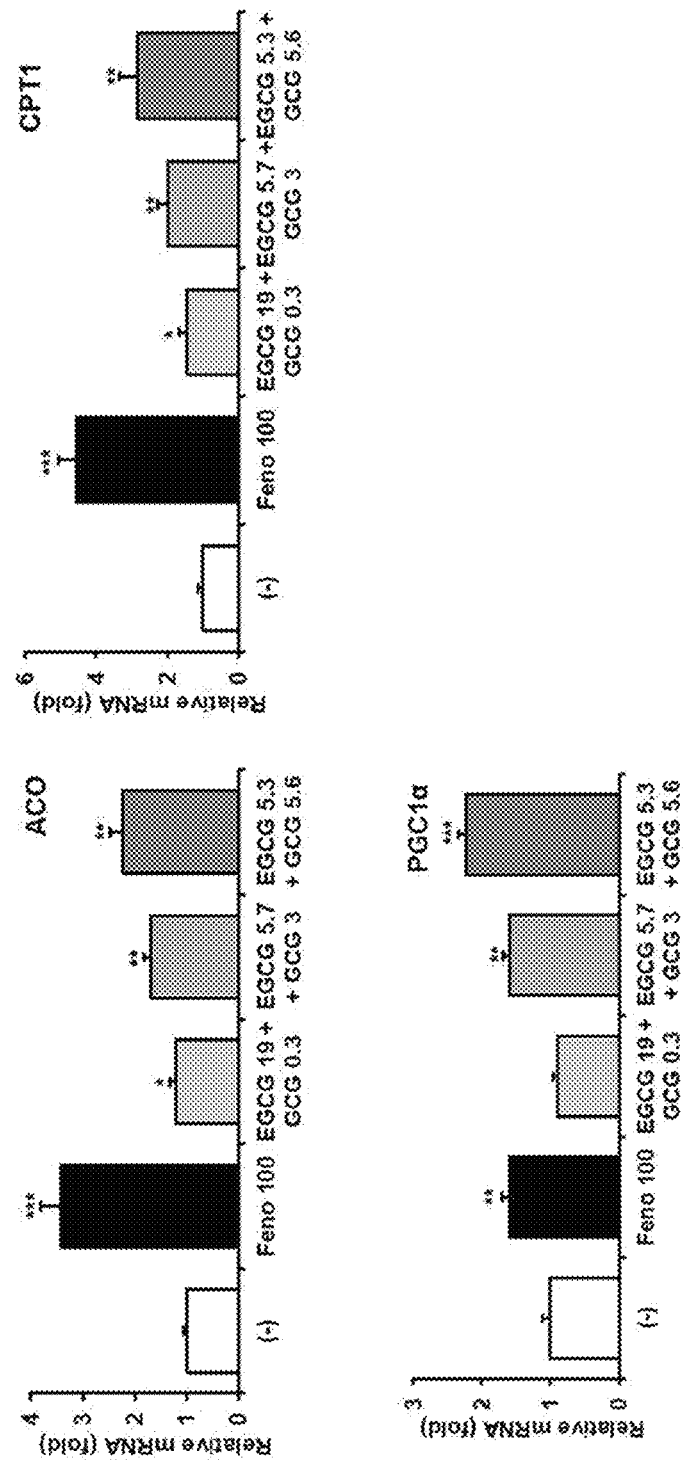
FIG. 7 shows a result of evaluating the fatty acid oxidation gene expression-increasing effect of the ingredients of a green tea extract.

The result of quantifying the expression level of fatty acid oxidation-associated genes (PGC-1α, ACO and CPT1) according to the method of Reference Example 2 is shown in FIG. 7 (*$P<0.001$ vs. (−), $P<0.01$ vs. (−), *$P<0.05$ vs. (−)).

2. Evaluation Result

As seen from FIG. 7, the treatment with the heat-transformed green tea extract (HTGT) of the present disclosure showed superior effect of increasing the expression of the fatty acid oxidation genes. Thus, it seems that the result of Test Example 7 is caused by the contents and ratio of gallocatechin gallate (GCG) and epigallocatechin gallate (EGCG) in the heat-transformed green tea extract (HTGT) of the present disclosure.

<Test Example 9> Evaluation of Fatty Acid Oxidation Gene Expression-Increasing Effect of Green Tea Extract 3

As seen from Table 2, the total catechin content of the green tea extract (GTE) was 40.4 wt %, and the total catechin content of the heat-transformed green tea extract (HTGT) was 24.6 wt %. Thus, after making correction such that the total catechin content of the green tea extract (GTE) was equal to the total catechin content of the heat-transformed green tea extract (HTGT) (24.6/40.4≈0.61), experiment was conducted as follows.

1. Evaluation Method

The adipocytes differentiated as in Reference Example 1 were treated with the green tea extract (GTE) prepared in Preparation Example 1 at 61 or 100 μg/mL (GTE 61 or GTE 100) for 24 hours, or with the heat-transformed green tea extract (HTGT) at 100 μg/mL (HTGT 100) for 24 hours. A control group for comparison was treated with 30 μM fenofibrate (Feno) which inhibits fat synthesis and facilitates fatty acid oxidation. A negative control group was treated with a vehicle (distilled water).

Figure 8:
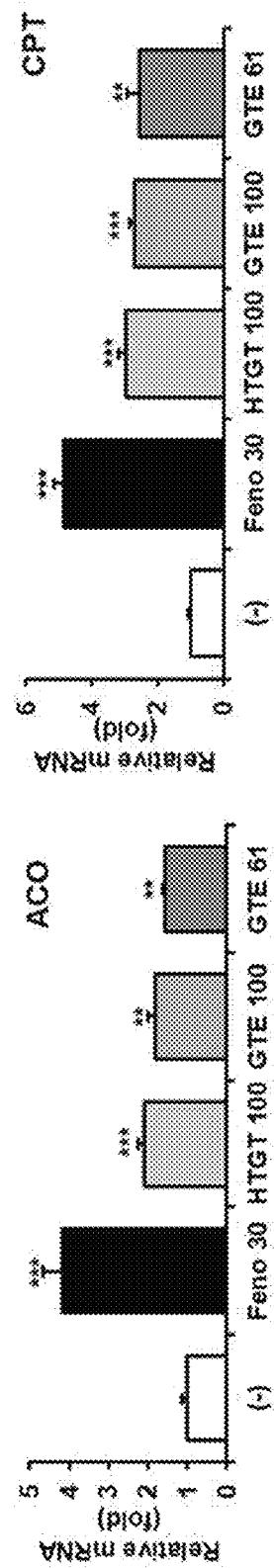

The result of quantifying the expression level of fatty acid oxidation-associated genes (ACO and CPT1) according to the method of Reference Example 2 is shown in FIG. 8 (*$P<0.001$ vs. (−), $P<0.01$ vs. (−), *$P<0.05$ vs. (−)).

2. Evaluation Result

As seen from FIG. 8, the treatment with the heat-transformed green tea extract (HTGT) of the present disclosure showed superior effect of increasing the expression of the fatty acid oxidation genes as compared to the treatment with the green tea extract (GTE). In addition, when correction was made such that the total catechin content of the green tea extract (GTE) was equal to the total catechin content of the heat-transformed green tea extract (HTGT), the treatment with the heat-transformed green tea extract (HTGT) of the present disclosure showed better effect of inhibiting the expression of the lipid synthesis genes as compared to the treatment with the green tea extract (GTE).

<Test Example 10> Evaluation of Triglyceride Degradation-Facilitating Effect of Green Tea Extract 1. Evaluation Method The adipocytes differentiated as in Reference Example 1 were treated with the heat-transformed green tea extract (HTGT) prepared in Preparation Example 1 at 10, 50 or 100 μg/mL (HTGT 10, HTGT 50 or HTGT 100) for 4 hours. A control group for comparison was treated with 500 μM 3-isobutyl-1-methylxanthine (IBMX) which induces fat degradation. A negative control group was treated with a vehicle (distilled water).

The degree of fat degradation was measured by quantifying the amount of glycerol produced from degradation of triglycerides using glycerol reagent (Sigma-Aldrich). The result is shown in FIG. 9 (***$P<0.001$ vs. (−)).

2. Evaluation Result

Figure 9:
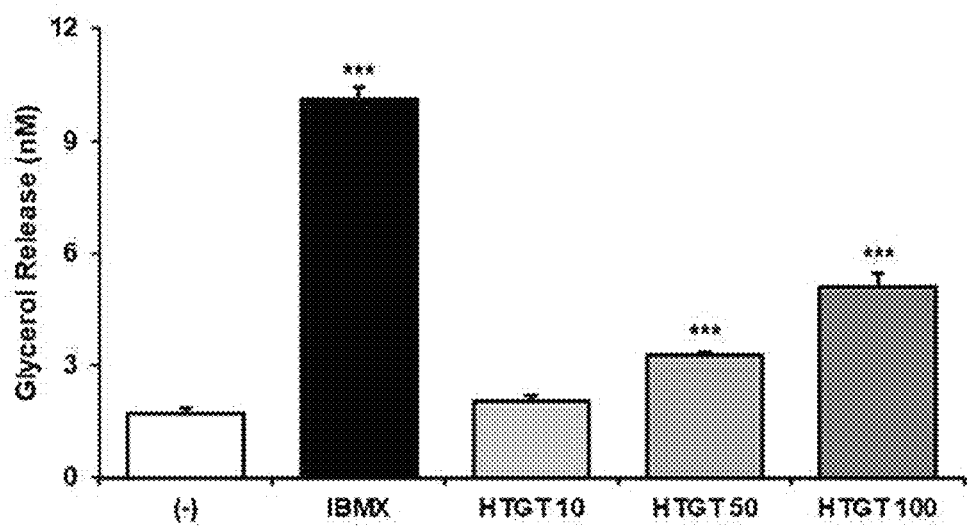
FIG. 9 shows a result of evaluating the triglyceride degradation-facilitating effect of a green tea extract.

As seen from FIG. 9, it was confirmed that the treatment with the heat-transformed green tea extract (HTGT) of the present disclosure had an effect of facilitating the degradation of triglycerides in adipocytes in a concentration-dependent manner as in the IBMX-treated control group.

<Test Example 11> Evaluation of Mitochondrial Activation and ATP Production-Facilitating Effect of Green Tea Extract 1

1. Evaluation Method

The adipocytes differentiated as in Reference Example 1 were treated with the heat-transformed green tea extract (HTGT) prepared in Preparation Example 1 at 10, 50 or 100 μg/mL (HTGT 10, HTGT 50 or HTGT 100) for 24 hours. A control group for comparison was treated with 30 μM fenofibrate (Feno) which inhibits fat synthesis and facilitates fatty acid oxidation. A negative control group was treated with a vehicle (distilled water).

Then, mitochondria were quantified by measuring fluorescence after staining using the MitoTracker™ Green FM (Invitrogen by Thermo Fisher Scientific) dye. Meanwhile, in order to investigate whether energy production is facilitated with the increased number of the mitochondria, the intracellular amount of ATP was measured using an ATP assay kit (Sigma-Aldrich). The result is shown in FIG. 10 (*$P<0.001$ vs. (−), $P<0.01$ vs. (−)).

2. Evaluation Result

Figure 10:
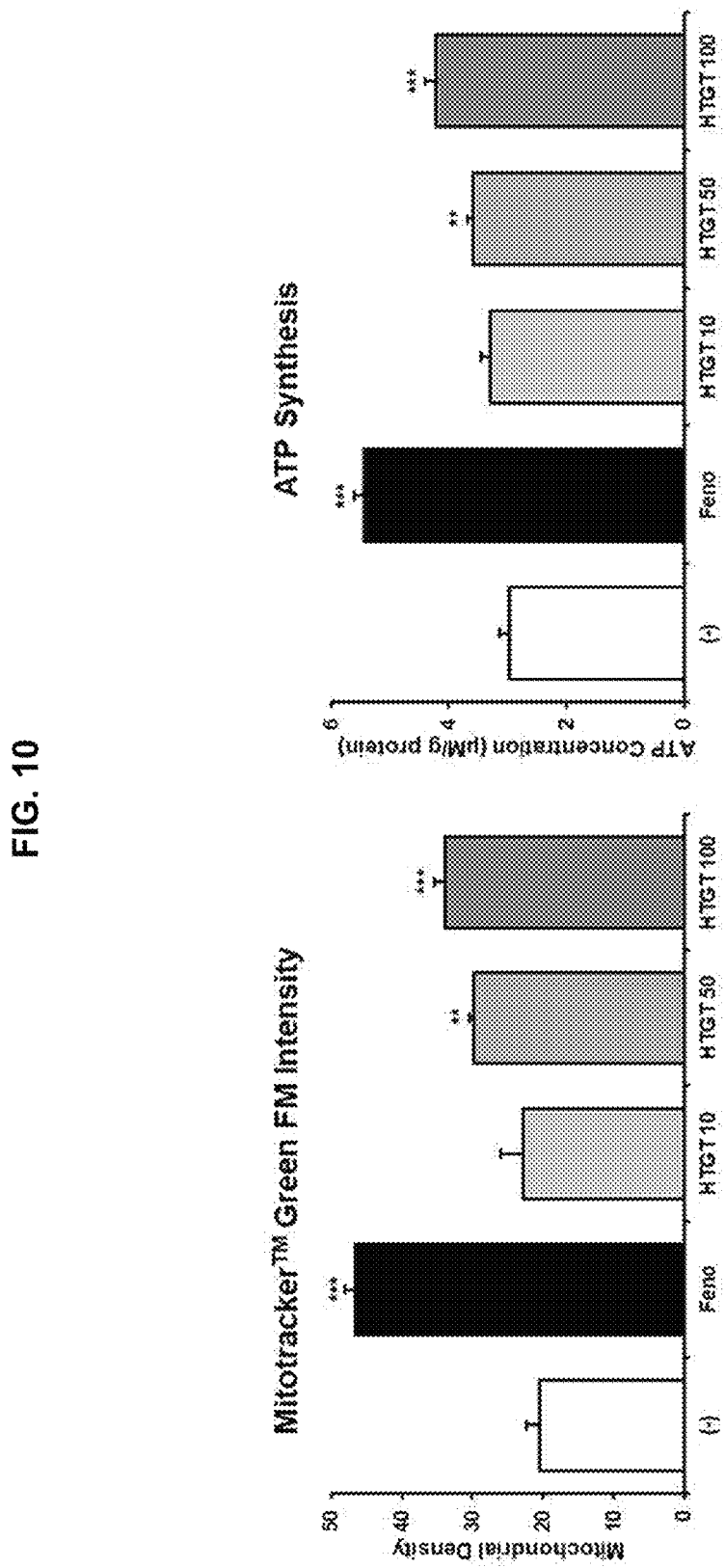
FIGS. 10, 11 and 13 show a result of evaluating the mitochondrial activation-facilitating effect and ATP production-facilitating effect of a green tea extract.

As seen from FIG. 10, it was confirmed that the treatment with the heat-transformed green tea extract (HTGT) of the present disclosure increases the amount and activity of mitochondria and facilitates ATP production in adipocytes. From this, it is expected that the composition of the present disclosure will exhibit superior slimming effect by maximizing energy production following fat degradation and burning.

<Test Example 12> Evaluation of Mitochondrial Activation and ATP Production-Facilitating Effect of Green Tea Extract 2

Experiment was performed as follows to compare the mitochondrial activation-facilitating effect and ATP production-facilitating effect of the heat-transformed green tea extract (HTGT) of the present disclosure with the green tea extract (GTE) and the fermented green tea extract (FGT).

1. Evaluation Method

The adipocytes differentiated as in Reference Example 1 were treated with the green tea extract (GTE) prepared in Preparation Example 1, the fermented green tea extract (FGT) or the heat-transformed green tea extract (HTGT) at 100 µg/mL (GTE 100, FGT 100 or HTGT 100) for 24 hours. A control group for comparison was treated with 100 µM fenofibrate (Feno) which inhibits fat synthesis and facilitates fatty acid oxidation. A negative control group was treated with a vehicle (distilled water).

Then, mitochondria were quantified by measuring fluorescence after staining using the MitoTracker™ Green FM (Invitrogen by Thermo Fisher Scientific) dye. Meanwhile, in order to investigate whether energy production is facilitated with the increased number of the mitochondria, the intracellular amount of ATP was measured using an ATP assay kit (Sigma-Aldrich). The result is shown in FIG. 11 (*$P<0.001$ vs. (−), $P<0.01$ vs. (−), *$P<0.05$ vs. (−)).

2. Evaluation Result

Figure 11:
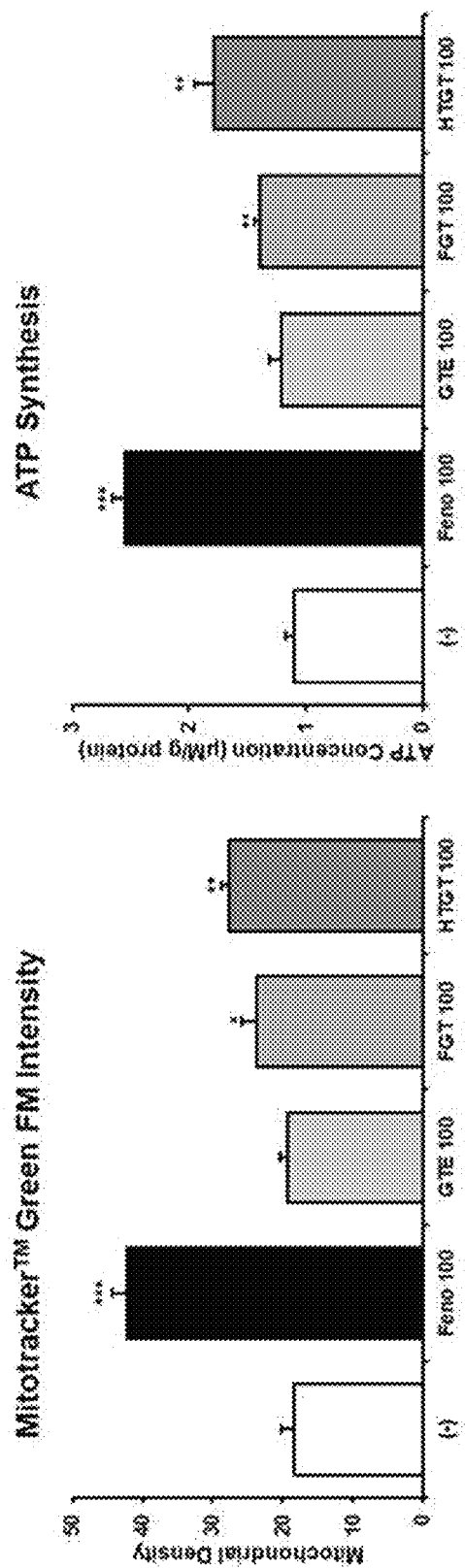

As seen from FIG. 11, it was confirmed that the treatment with the heat-transformed green tea extract (HTGT) of the present disclosure has the superior effect of increasing the amount and activity of mitochondria and facilitating ATP production in adipocytes as compared to the treatment with the green tea extract (GTE) or the fermented green tea extract (FGT).

<Test Example 13> Evaluation of Mitochondrial Activation and ATP Production-Facilitating Effect of Ingredients of Green Tea Extract Experiment was performed as follows to compare the mitochondrial activation-facilitating effect and ATP production-facilitating effect depending on the contents and ratio of gallocatechin gallate (GCG) and epigallocatechin gallate (EGCG) in the green tea extract.

1. Evaluation Method

The adipocytes differentiated as in Reference Example 1 were treated with the green tea extract (GTE), the fermented green tea extract (FGT) or the heat-transformed green tea extract (HTGT), containing gallocatechin gallate (GCG) and epigallocatechin gallate (EGCG) as described in Table 2, for 24 hours (GTE: GCG 0.3 wt %, EGCG 19.0 wt %; FGT: GCG 3.0 wt %, EGCG 5.7 wt %; HTGT: GCG 5.6 wt %, EGCG 5.3 wt %). A control group for comparison was treated with 100 µM fenofibrate (Feno) which inhibits fat synthesis and facilitates fatty acid oxidation. A negative control group was treated with a vehicle (distilled water).

Then, mitochondria were quantified by measuring fluorescence after staining using the MitoTracker™ Green FM (Invitrogen by Thermo Fisher Scientific) dye. Meanwhile, in order to investigate whether energy production is facilitated with the increased number of the mitochondria, the intracellular amount of ATP was measured using an ATP assay kit (Sigma-Aldrich). The result is shown in FIG. 12 (*$P<0.001$ vs. (−), $P<0.01$ vs. (−), *$P<0.05$ vs. (−)).

2. Evaluation Result

Figure 12:
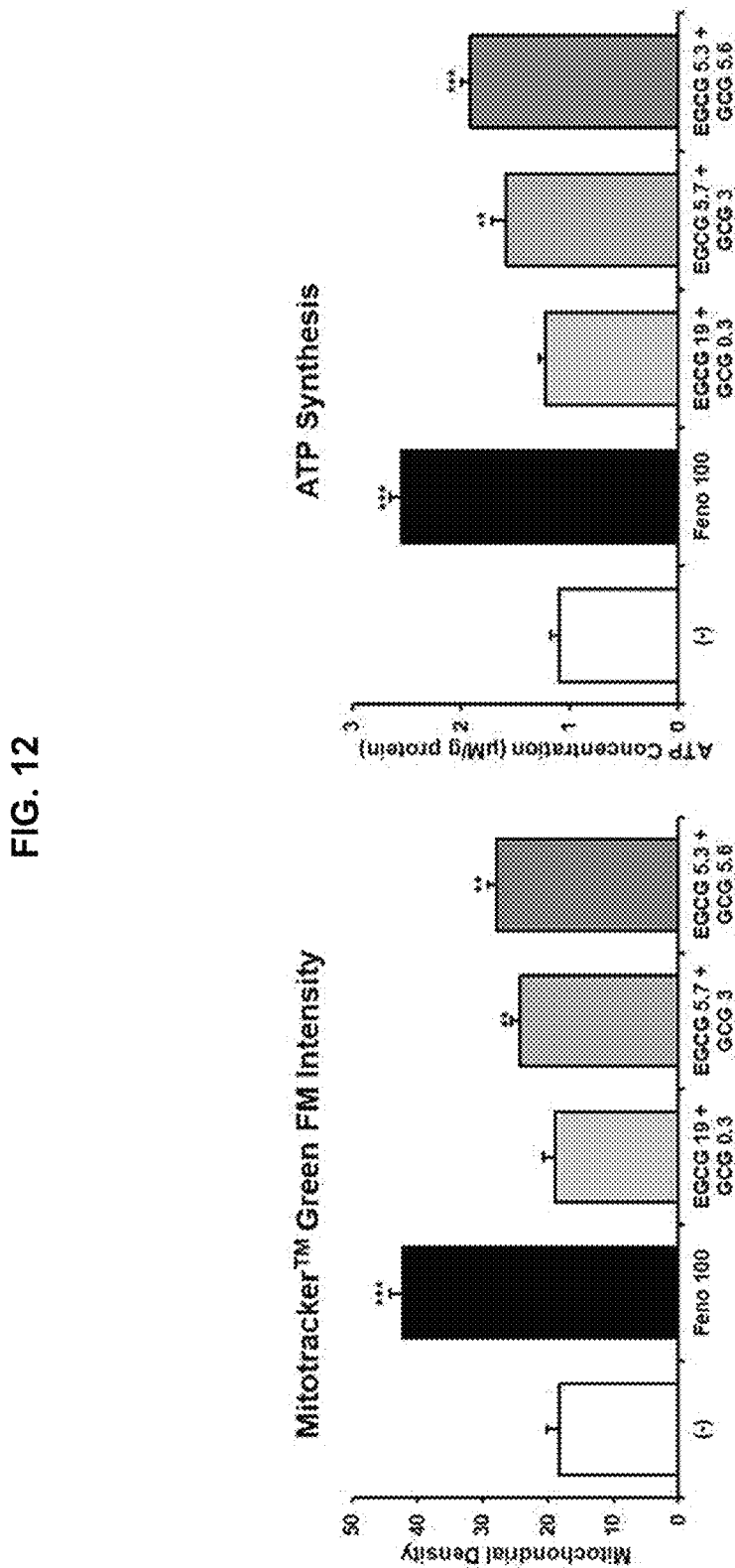
FIG. 12 shows a result of evaluating the mitochondrial activation-facilitating effect and ATP production-facilitating effect of the ingredients of a green tea extract.

As seen from FIG. 12, it was confirmed that the treatment with the heat-transformed green tea extract (HTGT) of the present disclosure increases the amount and activity of mitochondria and facilitates ATP production in adipocytes. From this, it is thought that the result of Test Example 12 is caused by the contents and ratio of gallocatechin gallate (GCG) and epigallocatechin gallate (EGCG) in the heat-transformed green tea extract (HTGT) of the present disclosure.

<Test Example 14> Evaluation of Mitochondrial Activation and ATP Production-Facilitating Effect of Green Tea Extract 3

As seen from Table 2, the total catechin content of the green tea extract (GTE) was 40.4 wt %, and the total catechin content of the heat-transformed green tea extract (HTGT) was 24.6 wt %. Thus, after making correction such that the total catechin content of the green tea extract (GTE) was equal to the total catechin content of the heat-transformed green tea extract (HTGT) (24.6/40.4≈0.61), experiment was conducted as follows.

1. Evaluation Method

The adipocytes differentiated as in Reference Example 1 were treated with the green tea extract (GTE) prepared in Preparation Example 1 at 61 or 100 µg/mL (GTE 61 or GTE 100) for 24 hours, or with the heat-transformed green tea extract (HTGT) at 100 µg/mL (HTGT 100) for 24 hours. A control group for comparison was treated with 30 µM fenofibrate (Feno) which inhibits fat synthesis and facilitates fatty acid oxidation. A negative control group was treated with a vehicle (distilled water).

Then, mitochondria were quantified by measuring fluorescence after staining using the MitoTracker™ Green FM (Invitrogen by Thermo Fisher Scientific) dye. Meanwhile, in order to investigate whether energy production is facilitated with the increased number of the mitochondria, the intracellular amount of ATP was measured using an ATP assay kit (Sigma-Aldrich). The result is shown in FIG. 13 (*$P<0.001$ vs. (−), $P<0.01$ vs. (−)).

2. Evaluation Result

Figure 13:
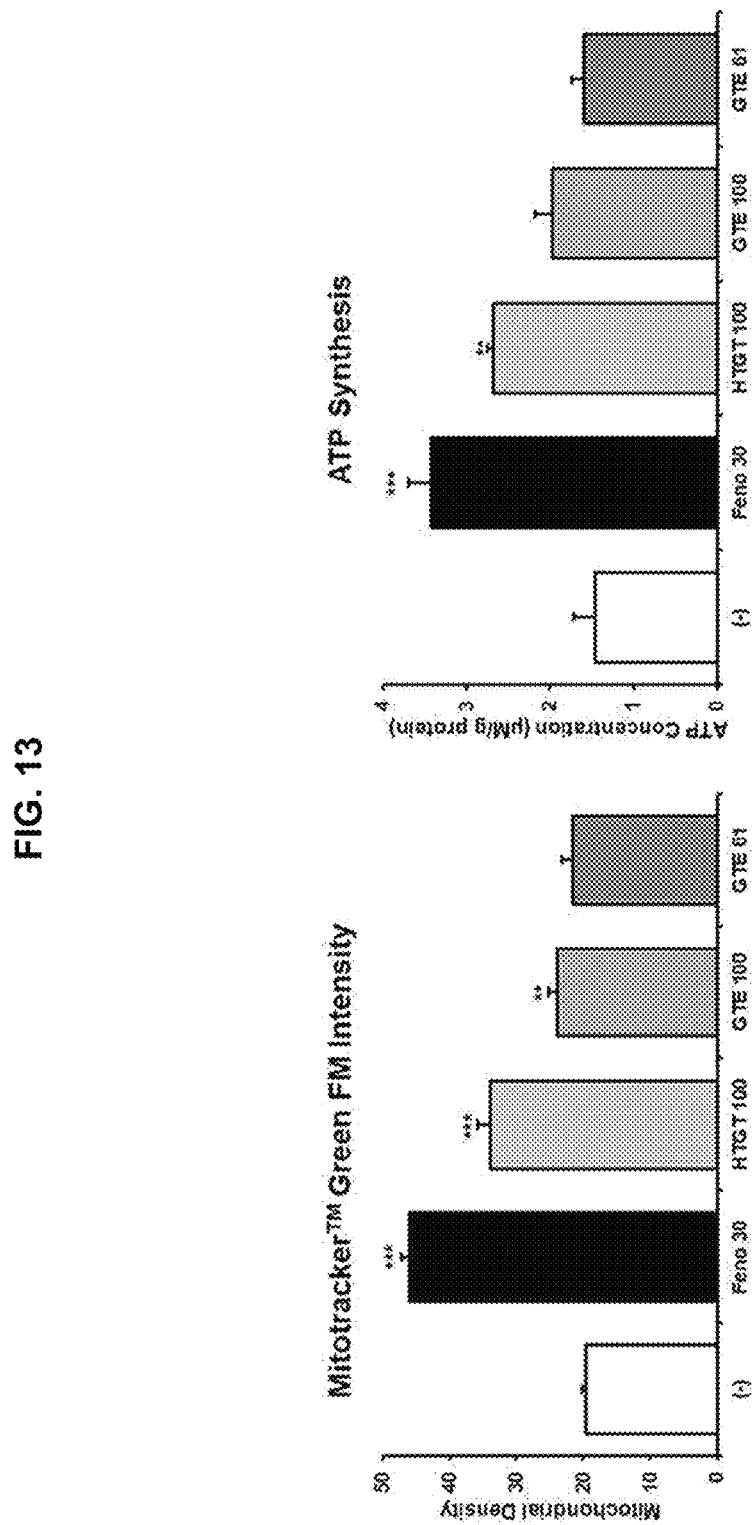

As seen from FIG. 13, the treatment with the heat-transformed green tea extract (HTGT) of the present disclosure showed superior effect of increasing the amount and activity of mitochondria and facilitating ATP production in adipocytes as compared to the treatment with the green tea extract (GTE). In addition, when correction was made such that the total catechin content of the green tea extract (GTE) was equal to the total catechin content of the heat-transformed green tea extract (HTGT), the treatment with the heat-transformed green tea extract (HTGT) of the present disclosure showed better effect of increasing the amount and activity of mitochondria and facilitating ATP production in adipocytes as compared to the treatment with the green tea extract (GTE).

<Test Example 15> Evaluation of Brown Adipocyte-Associated Gene Expression-Increasing Effect of Ingredients of Green Tea Extract 1

1. Evaluation Method

The adipocytes differentiated as in Reference Example 1 were treated with gallocatechin gallate (GCG), which was found to be contained in large quantities particularly in the heat-transformed green tea extract (HTGT) (Table 2), at 0.1, 1, 5, 10 or 20 µM for 24 hours. A negative control group was treated with a vehicle (distilled water).

Figure 14:
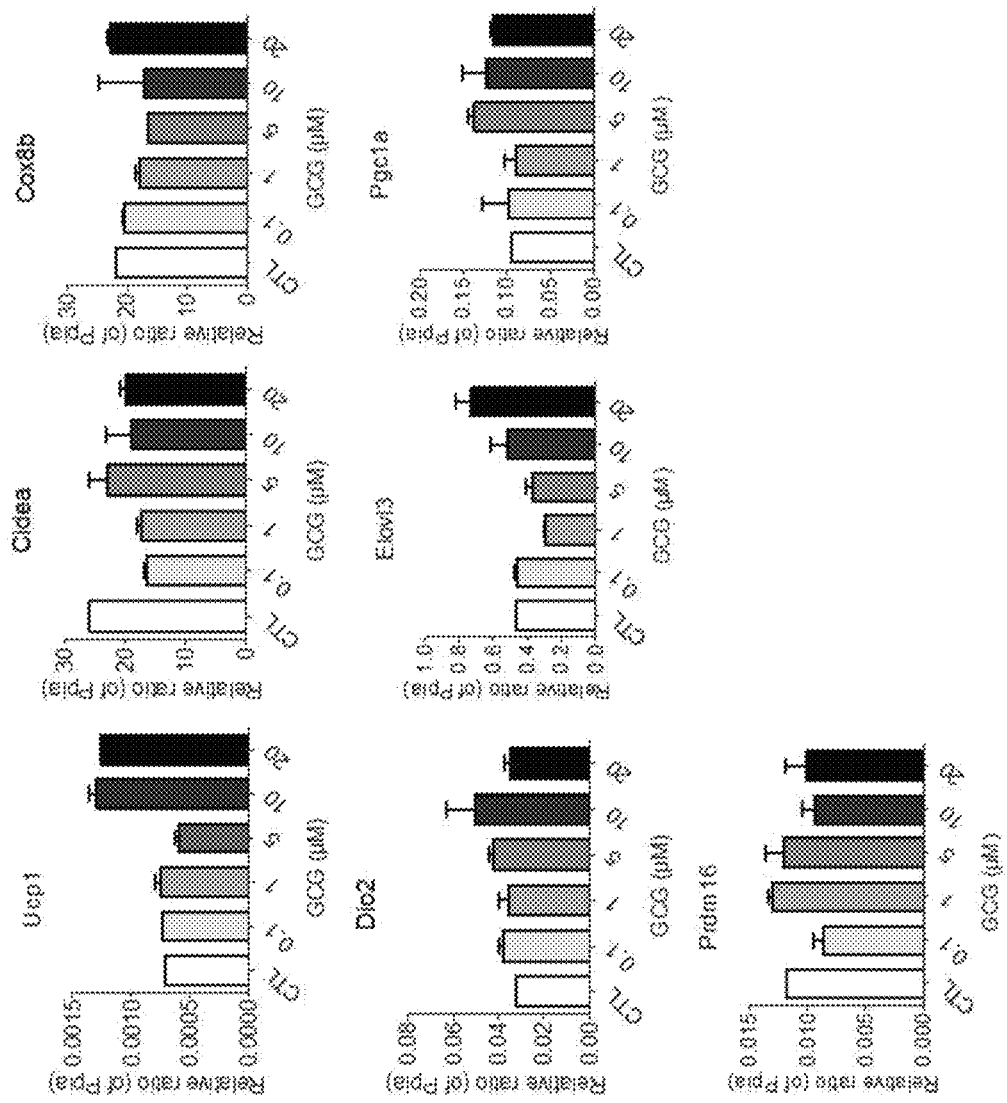
FIGS. 14 and 16 show a result of evaluating the brown adipocyte-associated gene expression-increasing effect of the ingredients of a green tea extract.

The result of quantifying the expression level of brown adipocyte-associated markers, Ucp1 (uncoupling protein 1), Cidea (cell death-inducing DFFA-like effector a), Cox8b (cytochrome c oxidase subunit 8B), Dio2 (iodothyronine deiodinase 2), Elovl3 (elongation of very long chain fatty acids), Pgc1a (peroxisome proliferator-activated receptor c coactivator 1a) and Prdm16 (PR domain containing 16), according to the method of Reference Example 2 is shown in FIG. 14 (*$P<0.001$ vs. (−), $P<0.01$ vs. (−), *$P<0.05$ vs. (−)).

2. Evaluation Result

As seen from FIG. 14, the treatment with gallocatechin gallate (GCG), which is contained in large quantities particularly in the heat-transformed green tea extract (HTGT) of the present disclosure, increased the expression of the fat degradation-associated Elovl3 and the uncoupling protein 1 (Ucp1), whereas the expression of Prdm16 associated with differentiation into brown adipocytes was not changed significantly. Therefore, it is thought that GCG induces the beige adipocyte transformation of white adipocytes through fat transformation rather than differentiation into brown adipocytes.

<Test Example 16> Evaluation of Brown Adipocyte-Associated Gene Expression-Increasing Effect of Green Tea Extract 1

Experiment was performed as follows to compare the brown adipocyte-associated gene expression-increasing effect of the heat-transformed green tea extract (HTGT) of the present disclosure with the green tea extract (GTE) and the fermented green tea extract (FGT).
1. Evaluation Method The adipocytes differentiated as in Reference Example 1 were treated with the green tea extract (GTE) prepared in Preparation Example 1, the fermented green tea extract (FGT) or the heat-transformed green tea extract (HTGT) at 100 μg/mL (GTE 100, FGT 100 or HTGT 100) for 24 hours. A control group for comparison was treated with 100 μM fenofibrate (Feno) which inhibits fat synthesis and facilitates fatty acid oxidation. A negative control group was treated with a vehicle (distilled water).

Figure 15:
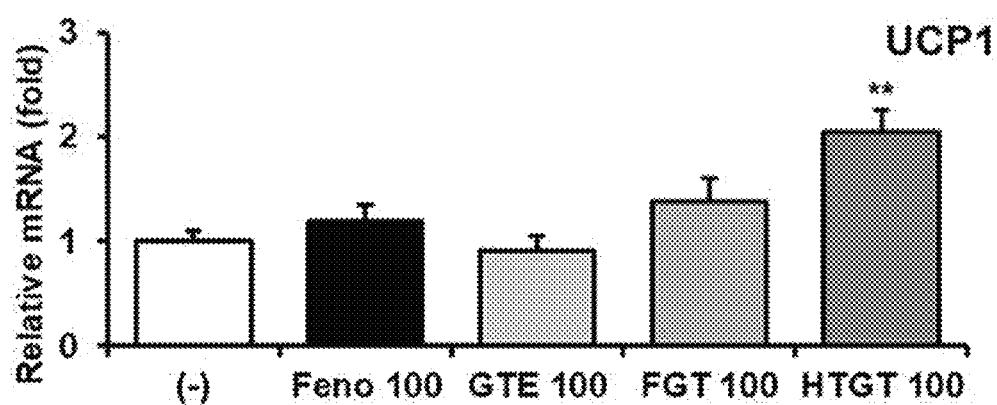
FIGS. 15 and 17 show a result of evaluating the brown adipocyte-associated gene expression-increasing effect of a green tea extract.

The result of quantifying the expression level of the brown adipocyte-associated marker Ucp1 (uncoupling protein 1) according to the method of Reference Example 2 is shown in FIG. 15 (*$P<0.001$ vs. (−), $P<0.01$ vs. (−), *$P<0.05$ vs. (−)).
2. Evaluation Result As seen from FIG. 15, the treatment with the heat-transformed green tea extract (HTGT) of the present disclosure showed superior effect of expressing uncoupling protein 1 (Ucp1) as compared to the treatment with the green tea extract (GTE) or the fermented green tea extract (FGT).

<Test Example 17> Evaluation of Brown Adipocyte-Associated Gene Expression-Increasing Effect of Ingredients of Green Tea Extract 2

Experiment was performed as follows to compare brown adipocyte-associated gene expression-increasing effect depending on the contents and ratio of gallocatechin gallate (GCG) and epigallocatechin gallate (EGCG) in the green tea extract.
1. Evaluation Method The adipocytes differentiated as in Reference Example 1 were treated with the green tea extract (GTE), the fermented green tea extract (FGT) or the heat-transformed green tea extract (HTGT), containing gallocatechin gallate (GCG) and epigallocatechin gallate (EGCG) as described in Table 2, for 24 hours (GTE: GCG 0.3 wt %, EGCG 19.0 wt %; FGT: GCG 3.0 wt %, EGCG 5.7 wt %; HTGT: GCG 5.6 wt %, EGCG 5.3 wt %). A control group for comparison was treated with 100 μM fenofibrate (Feno) which inhibits fat synthesis and facilitates fatty acid oxidation. A negative control group was treated with a vehicle (distilled water).

Figure 16:
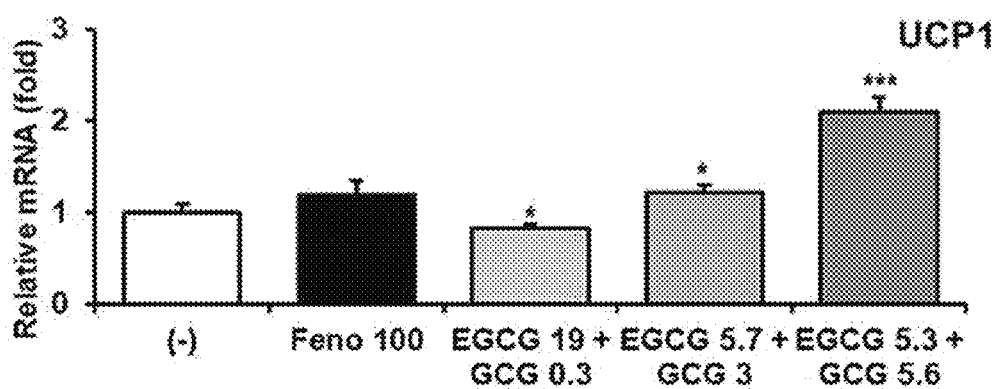

The result of quantifying the expression level of the brown adipocyte-associated marker Ucp1 (uncoupling protein 1) according to the method of Reference Example 2 is shown in FIG. 16 (*$P<0.001$ vs. (−), $P<0.01$ vs. (−), *$P<0.05$ vs. (−)).
2. Evaluation Result As seen from FIG. 16, the treatment with the heat-transformed green tea extract (HTGT) of the present disclosure showed superior effect of increasing the expression of uncoupling protein 1 (Ucp1). Thus, it seems that the result of Test Example 16 is caused by the contents and ratio of gallocatechin gallate (GCG) and epigallocatechin gallate (EGCG) in the heat-transformed green tea extract (HTGT) of the present disclosure.

<Test Example 18> Evaluation of Brown Adipocyte-Associated Gene Expression-Increasing Effect of Green Tea Extract 2

As seen from Table 2, the total catechin content of the green tea extract (GTE) was 40.4 wt %, and the total catechin content of the heat-transformed green tea extract (HTGT) was 24.6 wt %. Thus, after making correction such that the total catechin content of the green tea extract (GTE) was equal to the total catechin content of the heat-transformed green tea extract (HTGT) (24.6/40.4≈0.61), experiment was conducted as follows.
1. Evaluation Method The adipocytes differentiated as in Reference Example 1 were treated with the green tea extract (GTE) prepared in Preparation Example 1 at 61 or 100 μg/mL (GTE 61 or GTE 100) for 24 hours, or with the heat-transformed green tea extract (HTGT) at 100 μg/mL (HTGT 100) for 24 hours. A control group for comparison was treated with 30 μM fenofibrate (Feno) which inhibits fat synthesis and facilitates fatty acid oxidation. A negative control group was treated with a vehicle (distilled water).

Figure 17:
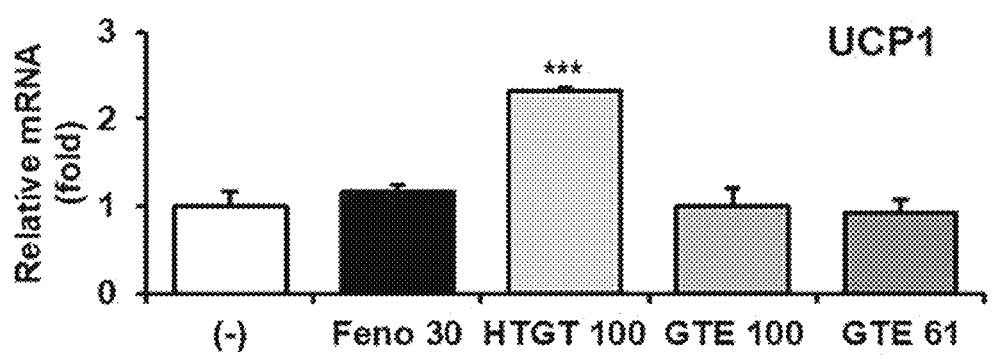

The result of quantifying the expression level of the brown adipocyte-associated marker Ucp1 (uncoupling protein 1) according to the method of Reference Example 2 is shown in FIG. 17 (*$P<0.001$ vs. (−), $P<0.01$ vs. (−), *$P<0.05$ vs. (−)).
2. Evaluation Result As seen from FIG. 17, the treatment with the heat-transformed green tea extract (HTGT) of the present disclosure showed superior effect of increasing the expression of uncoupling protein 1 (Ucp1) as compared to the treatment with the green tea extract (GTE). In addition, when correction was made such that the total catechin content of the green tea extract (GTE) was equal to the total catechin content of the heat-transformed green tea extract (HTGT), the treatment with the heat-transformed green tea extract (HTGT) of the present disclosure showed better effect of increasing the expression of uncoupling protein 1 (Ucp1) as compared to the treatment with the green tea extract (GTE).

<Test Example 19> Evaluation of Energy Metabolism Activity-Facilitating Effect in Adipocytes of Green Tea Extract Experiment was performed as follows to investigate whether gallocatechin gallate (GCG), which is contained in large quantities particularly in the heat-transformed green tea extract (HTGT) of the present disclosure, can actually increase the aerobic respiration of cells.
1. Evaluation Method The adipocytes differentiated as in Reference Example 1 were treated with 20 μM gallocatechin gallate (GCG), which is contained in large quantities particularly in the heat-transformed green tea extract (HTGT) (Table 2), for 24 hours. A negative control group was treated with a vehicle (distilled water).

Then, oxygen level and oxygen consumption rate (OCR) were measured using an XF analyzer (Agilent, Santa Clara, CA, USA). More specifically, 1.5 µM oligomycin A, 1.5 µM carbonyl cyanide p-(trifluoromethoxy)phenylhydrazone (FCCP) and 0.5 µM rotenone/antimycin A were injected sequentially at different time points A, B and C.

OCR was normalized to protein level. OCR, ATP production and proton leak with time are shown in FIG. 18 (*$P<0.001$,  $P<0.01$, * $P<0.05$).

2. Evaluation Result

Figure 18:
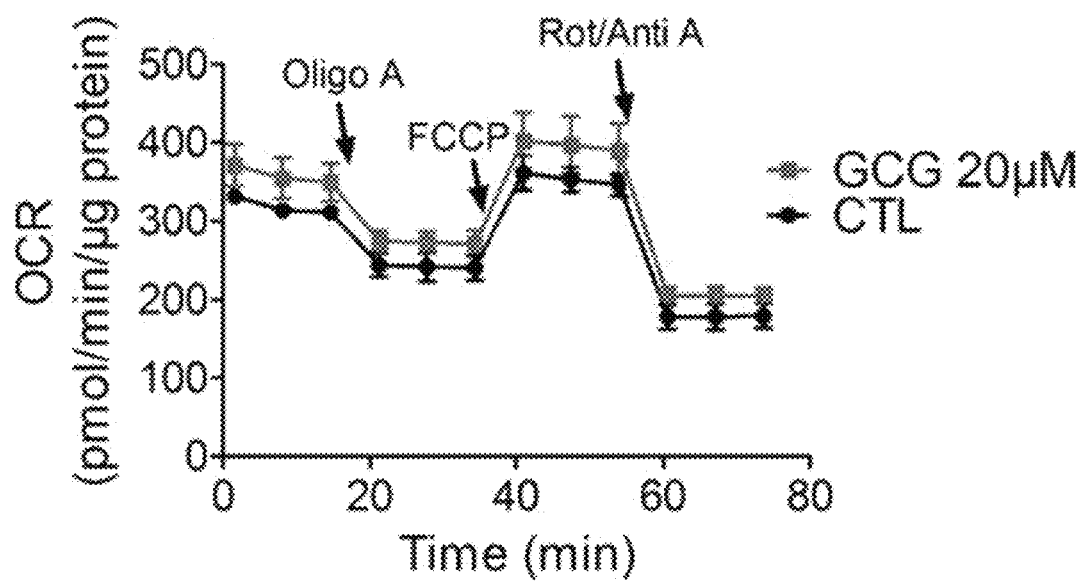
FIG. 18 shows a result of evaluating energy metabolism activity-facilitating effect in adipocytes of a green tea extract.
Figure 18:
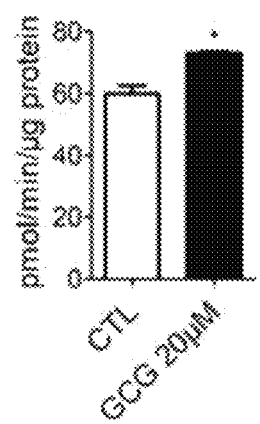
Figure 18:
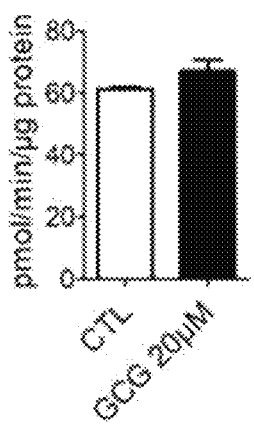

As seen from FIG. 18, the treatment with gallocatechin gallate (GCG) increased OCR regardless of the treatment with the drugs that regulate mitochondrial activity (oligomycin, FCCP and rotenone/antimycin A) and, as a result of the cellular respiration, both energy production (ATP production) and energy uncoupling (proton leak) were increased. Through this, it was confirmed that the treatment with gallocatechin gallate (GCG) actually increases aerobic respiration in adipocytes.

Hereinafter, formulation examples of the composition according to the present disclosure are described. However, the pharmaceutical composition and food composition according to the present disclosure can be prepared into various other formulations without being limited to the following examples.

[Formulation Example 1] Preparation of Pill

A pill was prepared according to the composition described in Table 3 by a common method.

TABLE 3

| Ingredients | Contents (wt %) |
|---|---|
| Heat-transformed green tea extract (HTGT) | 24 |
| Cornstarch | 30 |
| Glycerin | 20 |
| Sorbitol powder | 26 |

[Formulation Example 2] Preparation of Tablet

A tablet was prepared according to the composition described in Table 4 by a common method.

TABLE 4

| Ingredients | Contents (wt %) |
|---|---|
| Heat-transformed green tea extract (HTGT) | 24 |
| Lactose | 20.5 |
| Dextrin | 20 |
| Maltitol powder | 20 |
| Xylitol powder | 13 |
| Sugar ester | 2.5 |

[Formulation Example 3] Preparation of Granule

A granule was prepared according to the composition described in Table 5 by a common method.

TABLE 5

| Ingredients | Contents (wt %) |
|---|---|
| Heat-transformed green tea extract (HTGT) | 24 |
| Xylitol | 11 |
| Isomalt | 65 |

[Formulation Example 4] Preparation of Injection

An injection was prepared according to the composition described in Table 6 by a common method.

TABLE 6

| Ingredients | Contents (wt %) |
|---|---|
| Heat-transformed green tea extract (HTGT) | 8-40 |
| Sterilized distilled water for injection | Adequate |
| pH control agent | Adequate |

[Formulation Example 5] Preparation of Drink

A drink was prepared according to the composition described in Table 7 by a common method.

TABLE 7

| Ingredients | Contents (wt %) |
|---|---|
| Heat-transformed green tea extract (HTGT) | 0.08 |
| Glucose | 10 |
| Citric acid | 2 |
| Purified water | 188 |

The present disclosure relates to and includes at least the following embodiments.

[Embodiment 1] A composition for reducing body fat, which contains a green tea extract containing 4 wt % or more of gallocatechin gallate (GCG) based on the total weight of the extract as an active ingredient.

[Embodiment 2] The composition according to the embodiment 1, wherein the green tea extract contains 4-15 wt % of the gallocatechin gallate based on the total weight of the extract.

[Embodiment 3] The composition according to the embodiment 1 or 2, wherein the green tea extract contains 4-15 wt % of epigallocatechin gallate (EGCG) based on the total weight of the extract.

[Embodiment 4] The composition according to any of the embodiments 1 to 3, the green tea extract contains epigallocatechin gallate and gallocatechin gallate at a weight ratio of 1:0.33-3.

[Embodiment 5] The composition according to any of the embodiments 1 to 4, wherein the green tea extract contains 19-30 wt % of catechin (C), epicatechin (EC), gallocatechin (GC), epigallocatechin (EGC), catechin gallate (CG), epicatechin gallate (ECG), gallocatechin gallate (GCG) and epigallocatechin gallate (EGCG) based on the total weight of the extract.

[Embodiment 6] The composition according to any of the embodiments 1 to 5, wherein the composition is a composition for facilitating the degradation of triglycerides in adipocytes.

[Embodiment 7] The composition according to any of the embodiments 1 to 6, wherein the composition increases the expression of one or more fatty acid oxidation gene selected from a group consisting of PGC-1α, ACO, CPT1 and mCAD.

[Embodiment 8] The composition according to any of the embodiments 1 to 7, wherein the composition reduces the size of adipocytes.

[Embodiment 9] The composition according to any of the embodiments 1 to 8, wherein the composition is composition for inhibiting the synthesis or accumulation of triglycerides in adipocytes.

[Embodiment 10] The composition according to any of the embodiments 1 to 9, wherein the composition inhibits the expression of one or more lipid synthesis gene selected from a group consisting of SREBP1c, ACC, FAS and SCD-1.

[Embodiment 11] The composition according to any of the embodiments 1 to 10, wherein the composition is a composition for facilitating the activation of mitochondria in adipocytes.

[Embodiment 12] The composition according to any of the embodiments 1 to 11, wherein the composition is a composition for increasing basal metabolic rate.

[Embodiment 13] The composition according to any of the embodiments 1 to 12, wherein the composition induces the conversion of white adipocytes to beige adipocytes.

[Embodiment 14] The composition according to any of the embodiments 1 to 13, wherein the composition is a pharmaceutical composition for preventing, alleviating or treating obesity.

[Embodiment 15] The composition according to any of the embodiments 1 to 14, wherein the composition is a food composition for preventing or alleviating obesity.

[Embodiment 16] The composition according to any of the embodiments 1 to 15, wherein the green tea extract is obtained by a high-temperature treatment step of treating green tea with steam at 75-100° C. under a pressure of 1-2 kgf/cm² for 1-7 hours.

[Embodiment 17] A method for preparing the composition according to any of the embodiments 1 to 13, including a high-temperature treatment step of treating green tea with steam at 75-100° C. under a pressure of 1-2 kgf/cm² for 1-7 hours Although the present disclosure has been described in relation to specific exemplary embodiments, various modifications or changes can be made thereto without departing from the subject matter and scope of the present disclosure. Accordingly, such modifications or changes will be included in the scope of the present disclosure defined in the appended claims.

The invention claimed is:

1. A method for reducing body fat, comprising administering a composition comprising a heat transformed green tea extract comprising 4 wt % or more of gallocatechin gallate (GCG) based on the total weight of the heat transformed green tea extract to a subject in need thereof,
   wherein the heat transformed green tea extract is obtained by a high-temperature treatment step of treating a green tea extract at a treatment temperature of 75-100° C. by steam under a pressure of 1-2 kgf/cm² for 1-7 hours,
   wherein the heat transformed green tea extract comprises catechin (C), epicatechin (EC), gallocatechin (GC), epigallocatechin (EGC), catechin gallate (CG), epicatechin gallate (ECG), gallocatechin gallate (GCG), and epigallocatechin gallate EGCG),
   wherein the heat transformed green tea extract comprises epigallocatechin gallate and gallocatechin gallate at a weight ratio of 1:0.33-3, and
   wherein the heat transformed green tea extract comprises 4-15% wt. % of epigallocatechin gallate (EGCG) based on the total weight of the heat transformed green tea extract.

2. The method according to claim 1, wherein the heat transformed green tea extract comprises 4-15 wt % of the gallocatechin gallate based on the total weight of the heat transformed extract.

3. The method according to claim 1, wherein the heat transformed green tea extract comprises 19-30 wt % of catechin (C), epicatechin (EC), gallocatechin (GC), epigallocatechin (EGC), catechin gallate (CG), epicatechin gallate (ECG), gallocatechin gallate (GCG) and epigallocatechin gallate (EGCG) based on the total weight of the heat transformed green tea extract.

4. The method according to claim 1, wherein the reducing body fat is by facilitating the degradation of triglycerides in adipocytes.

5. The method according to claim 1, wherein the reducing body fat is by increasing the expression of one or more fatty acid oxidation gene selected from a group consisting of PGC-1α, ACO, CPT1 and mCAD.

6. The method according to claim 1, wherein the reducing body fat is by reducing the size of adipocytes.

7. The method according to claim 1, wherein the reducing body fat is by inhibiting the synthesis or accumulation of triglycerides in adipocytes.

8. The method according to claim 1, wherein the reducing body fat is by inhibiting the expression of one or more lipid synthesis gene selected from a group consisting of SREBP1c, ACC, FAS and SCD-1.

9. The method according to claim 1, wherein the reducing body fat is by facilitating the activation of mitochondria in adipocytes.

10. The method according to claim 1, wherein the reducing body fat is by increasing basal metabolic rate.

11. The method according to claim 1, wherein the reducing body fat is by inducing the conversion of white adipocytes to beige adipocytes.

12. The method according to claim 1, wherein the composition is a pharmaceutical composition for preventing, alleviating or treating obesity.

13. The method according to claim 1, wherein the composition is a food composition for preventing or alleviating obesity.

* * * * *